(12) United States Patent
Sadri et al.

(10) Patent No.: US 10,343,165 B2
(45) Date of Patent: Jul. 9, 2019

(54) ON-DEMAND PARTICLE DISPENSING SYSTEM

(71) Applicant: Bio-Rad Laboratories, Inc., Hercules, CA (US)

(72) Inventors: Amir Sadri, Toronto (CA); Kun Guo, Hercules, CA (US); Daniel Y. Chu, Hercules, CA (US); Nenad Kircanski, Toronto (CA); Paul J. Patt, Danville, CA (US); Tal Rosenzweig, Toronto (CA)

(73) Assignee: Bio-Rad Laboratories, Inc., Hercules, CA (US)

( * ) Notice: Subject to any disclaimer, the term of this patent is extended or adjusted under 35 U.S.C. 154(b) by 317 days.

(21) Appl. No.: 15/396,175

(22) Filed: Dec. 30, 2016

(65) Prior Publication Data

US 2017/0128941 A1    May 11, 2017

Related U.S. Application Data

(63) Continuation-in-part of application No. 14/479,155, filed on Sep. 5, 2014, now Pat. No. 9,784,664, and a
(Continued)

(51) Int. Cl.
*G01N 1/18* (2006.01)
*G01N 1/00* (2006.01)
(Continued)

(52) U.S. Cl.
CPC ....... *B01L 3/502761* (2013.01); *B01L 3/0265* (2013.01); *B01L 3/502738* (2013.01); *B01L 3/502776* (2013.01); *C12Q 1/24* (2013.01); *G01N 15/1056* (2013.01); *G01N 15/1404* (2013.01); *G01N 15/1484* (2013.01); *B01L 2200/027* (2013.01);
(Continued)

(58) Field of Classification Search
CPC . B01D 21/00; B01L 3/00; G01N 1/18; G01N 1/00
USPC ....... 422/501, 502, 503, 504, 509, 521, 527; 436/43, 174, 177, 180
See application file for complete search history.

(56) References Cited

U.S. PATENT DOCUMENTS

| 4,743,361 A | 5/1988 | Schram |
| 4,756,427 A * | 7/1988 | Gohde ............... G01N 15/1404 209/3.1 |

(Continued)

FOREIGN PATENT DOCUMENTS

| CN | 101253401 A | 8/2008 |
| CN | 101644703 A | 2/2010 |

(Continued)

OTHER PUBLICATIONS

Godin, Jessica et al., "Microfluidics and photonics for Bio-System-on-a-Chip: A review of advancements in technology towards a microfluidic flow cytometry chip", Journal of Biophotonics, vol. 1, No. 5, Oct. 2008, pp. 355-376.

(Continued)

*Primary Examiner* — Brian J. Sines
(74) *Attorney, Agent, or Firm* — Kolisch Hartwell, P.C.

(57) ABSTRACT

Systems, including apparatus and methods, for the microfluidic manipulation, dispensing, and/or sorting of particles, such as cells and/or beads.

16 Claims, 12 Drawing Sheets

Related U.S. Application Data continuation-in-part of application No. 14/479,132, filed on Sep. 5, 2014, now Pat. No. 9,535,000.

(60) Provisional application No. 61/902,664, filed on Nov. 11, 2013, provisional application No. 61/874,320, filed on Sep. 5, 2013.

(51) Int. Cl.
| | |
|---|---|
| *B01D 21/00* | (2006.01) |
| *B01L 3/00* | (2006.01) |
| *G01N 15/14* | (2006.01) |
| *B01L 3/02* | (2006.01) |
| *C12Q 1/24* | (2006.01) |
| *G01N 15/10* | (2006.01) |

(52) U.S. Cl.
CPC .......... *B01L 2200/0652* (2013.01); *B01L 2200/0689* (2013.01); *B01L 2200/12* (2013.01); *B01L 2200/146* (2013.01); *B01L 2200/147* (2013.01); *B01L 2200/16* (2013.01); *B01L 2300/021* (2013.01); *B01L 2300/044* (2013.01); *B01L 2300/0636* (2013.01); *B01L 2300/088* (2013.01); *B01L 2300/0816* (2013.01); *B01L 2300/0864* (2013.01); *B01L 2300/0887* (2013.01); *B01L 2300/123* (2013.01); *B01L 2300/16* (2013.01); *B01L 2300/165* (2013.01); *B01L 2300/18* (2013.01); *B01L 2400/0406* (2013.01); *B01L 2400/0409* (2013.01); *B01L 2400/0415* (2013.01); *B01L 2400/0457* (2013.01); *B01L 2400/0487* (2013.01); *B01L 2400/065* (2013.01); *B01L 2400/0644* (2013.01); *B01L 2400/0655* (2013.01); *B01L 2400/0688* (2013.01); *B01L 2400/082* (2013.01); *B01L 2400/084* (2013.01); *G01N 2015/1006* (2013.01); *G01N 2015/1081* (2013.01); *G01N 2015/149* (2013.01); *G01N 2015/1413* (2013.01); *Y10T 436/25* (2015.01); *Y10T 436/25375* (2015.01)

(56) References Cited

U.S. PATENT DOCUMENTS

| | | | |
|---|---|---|---|
| 5,638,961 A * | 6/1997 | Satake | B07C 5/3425 209/580 |
| 5,808,737 A | 9/1998 | Edens et al. | |
| 5,837,200 A | 11/1998 | Diessel et al. | |
| 6,540,895 B1 | 4/2003 | Spence et al. | |
| 6,657,713 B2 | 12/2003 | Hansen | |
| 6,877,528 B2 | 4/2005 | Gilbert et al. | |
| 7,258,774 B2 | 8/2007 | Chou et al. | |
| 7,311,476 B2 | 12/2007 | Gilbert et al. | |
| 7,389,879 B2 | 6/2008 | Tyvoll et al. | |
| 7,758,811 B2 | 7/2010 | Durack et al. | |
| 7,760,351 B2 | 7/2010 | Cox et al. | |
| 8,004,661 B2 | 8/2011 | Luscher | |
| 8,096,421 B2 | 1/2012 | Shinoda | |
| 8,871,500 B2 | 10/2014 | Foster et al. | |
| 9,109,197 B2 | 8/2015 | Yasuda et al. | |
| 2002/0176069 A1 * | 11/2002 | Hansen | G01N 15/147 356/73 |
| 2003/0027225 A1 | 2/2003 | Wada et al. | |
| 2003/0054558 A1 | 3/2003 | Kurabayashi et al. | |
| 2005/0134850 A1 * | 6/2005 | Rezachek | G01B 11/272 356/399 |
| 2007/0009386 A1 | 1/2007 | Padmanabhan et al. | |
| 2008/0213821 A1 | 9/2008 | Liu et al. | |
| 2008/0309919 A1 * | 12/2008 | Birmingham | G01N 15/065 356/72 |
| 2010/0112679 A1 * | 5/2010 | Vandergaw | G01N 35/1095 435/287.3 |
| 2010/0303687 A1 | 12/2010 | Blaga et al. | |
| 2011/0045993 A1 | 2/2011 | Kent et al. | |
| 2012/0009025 A1 | 1/2012 | Gilbert et al. | |
| 2012/0181460 A1 | 7/2012 | Eberhart et al. | |
| 2013/0171683 A1 * | 7/2013 | Durack | C12N 5/0612 435/29 |
| 2013/0224734 A1 * | 8/2013 | Durack | C12N 5/0612 435/6.1 |
| 2015/0064694 A1 | 3/2015 | Sadri et al. | |

FOREIGN PATENT DOCUMENTS

| | | |
|---|---|---|
| EP | 2153898 A1 | 2/2010 |
| WO | 2010144814 A2 | 12/2010 |

OTHER PUBLICATIONS

Klank, H. et al., "PIV measurements in a microfluidic 3D-sheathing structure with three-dimensional flow behaviour", Journal of Micromechanics and Microengineering, vol. 12, Oct. 3, 2002, pp. 862-869.

Wolff, A. et al., "Integrating advanced functionality in a microfabricated high-throughput fluorescent-activated cell sorter", Lab on a Chip, vol. 3, Jan. 23, 2003, pp. 22-27.

Copenheaver, Blaine R., Authorized Officer, International Searching Authority/US, Commissioner for Patents, "International Search Report" in connection with International Application No. PCT/US2014/054403, dated Dec. 22, 2014, 2 pages.

Copenheaver, Blaine R., Authorized Officer, International Searching Authority/US, Commissioner for Patents, "Written Opinion of the International Searching Authority" in connection with International Application No. PCT/US2014/054403, dated Dec. 22, 2014, 14 pages.

Grover, William H. et al., "Teflon films for chemically-inert microfluidic valves and pumps", Lab on a Chip vol. 8, Apr. 11, 2008, pp. 913-918.

Grover, William H. et al., "Monolithic membrane valves and diaphragm pumps for practical large-scale integration into glass microfluidic devices", Science Direct, Sensors and Actuators B, vol. 89, 2003, pp. 315-323.

European Patent Office, "Extended European Search Report" in connection with related European Patent Application No. 14841752.0, dated Mar. 6, 2017, 7 pages.

* cited by examiner

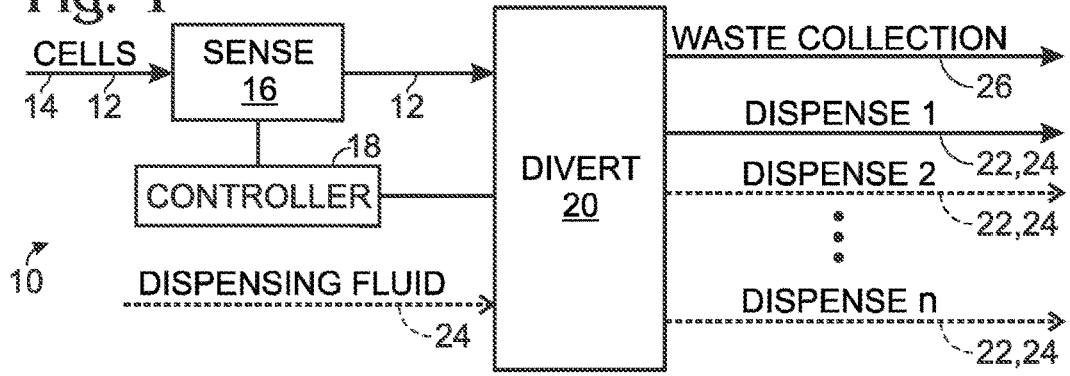
Fig. 1
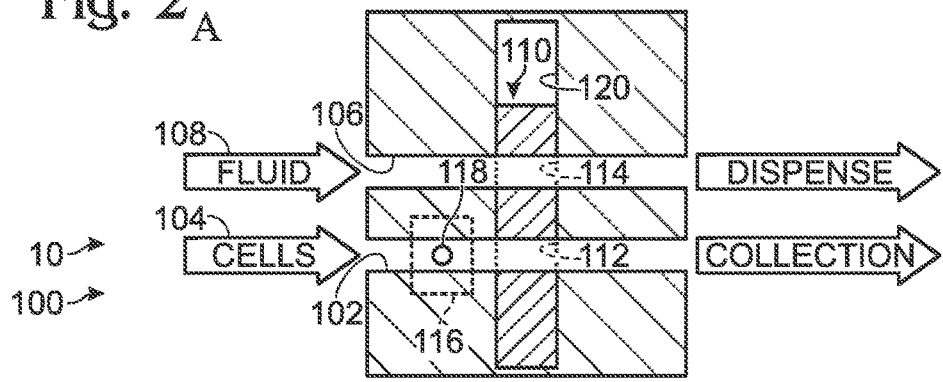
Fig. 2A
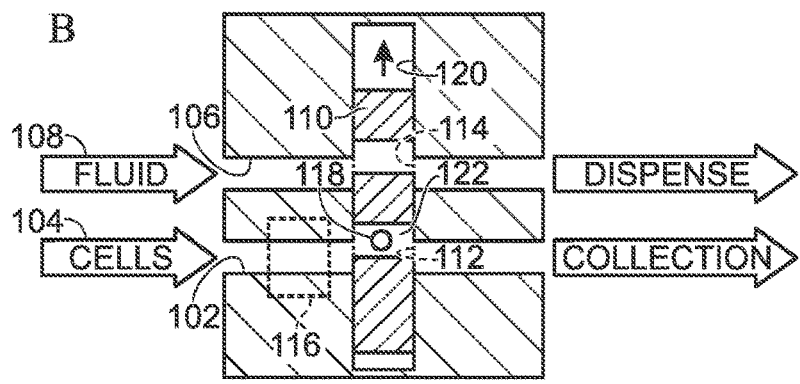
B
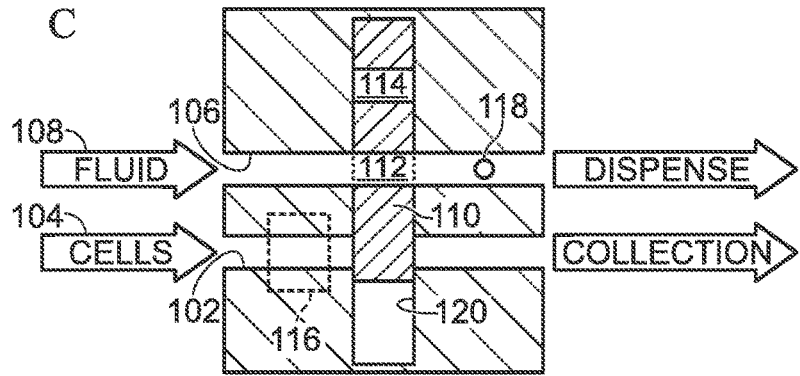
C

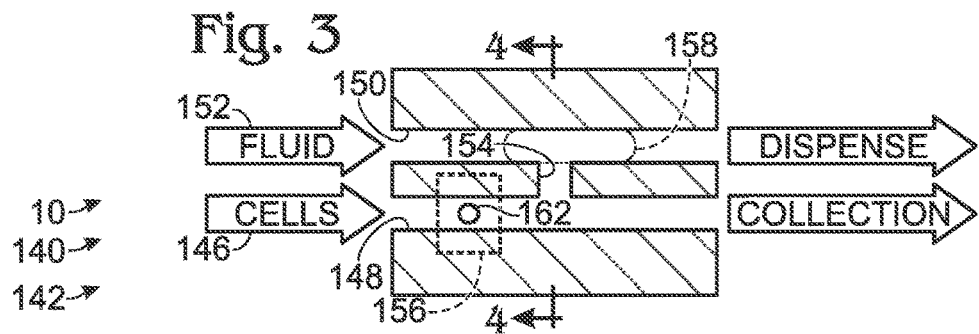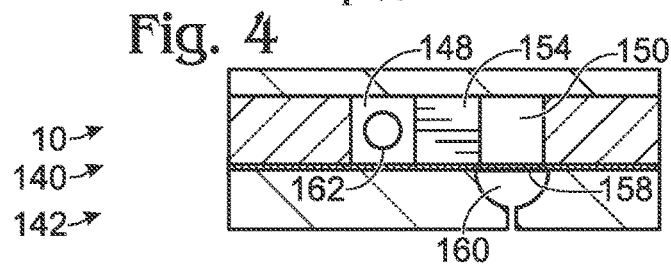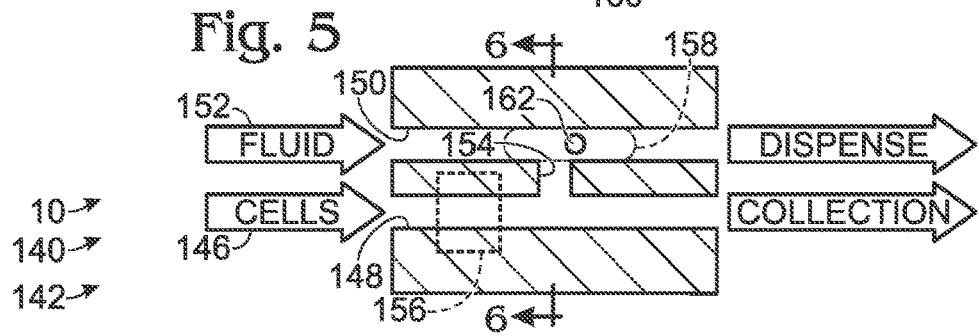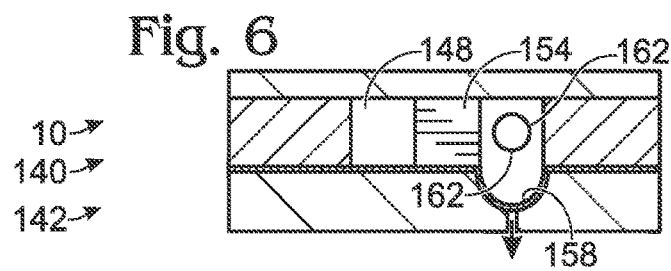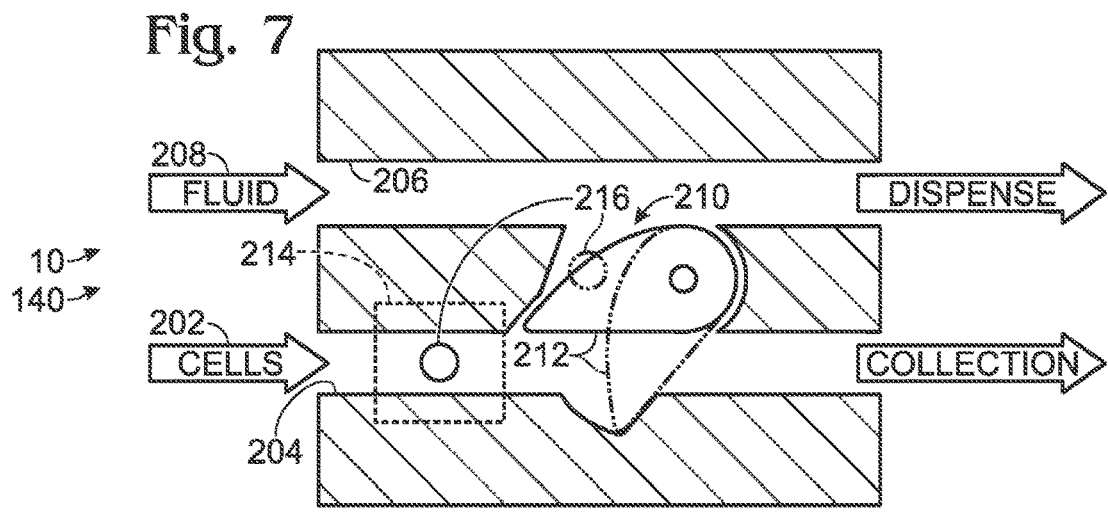

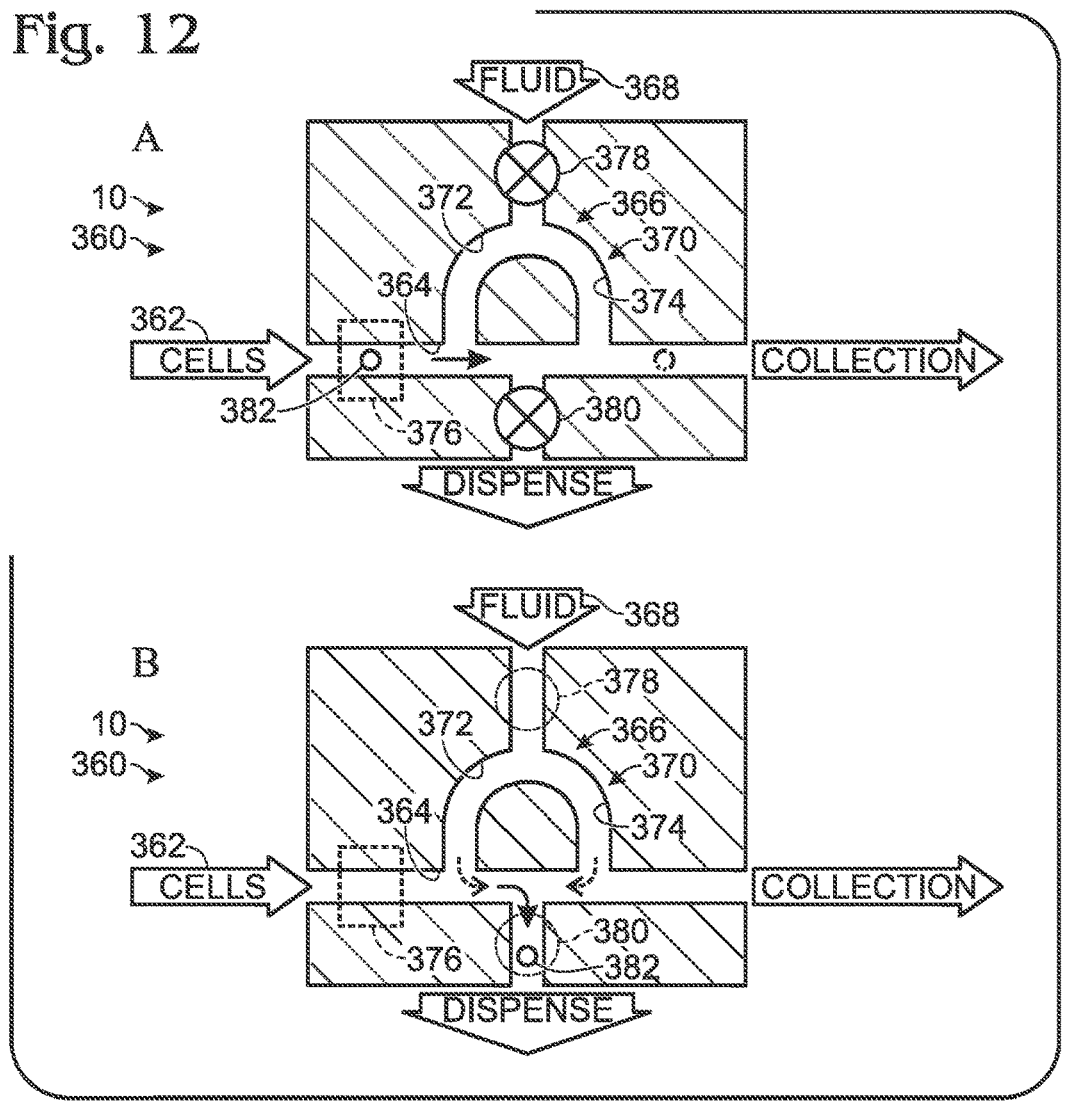
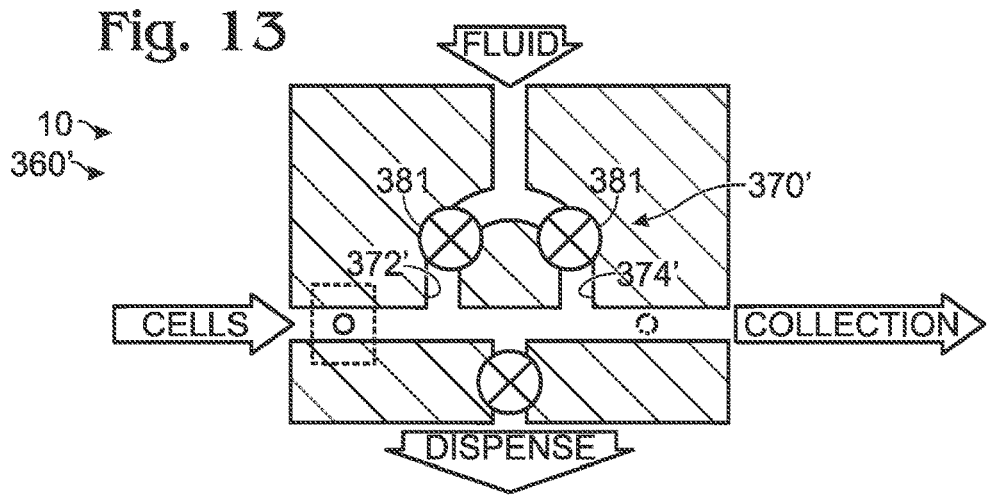

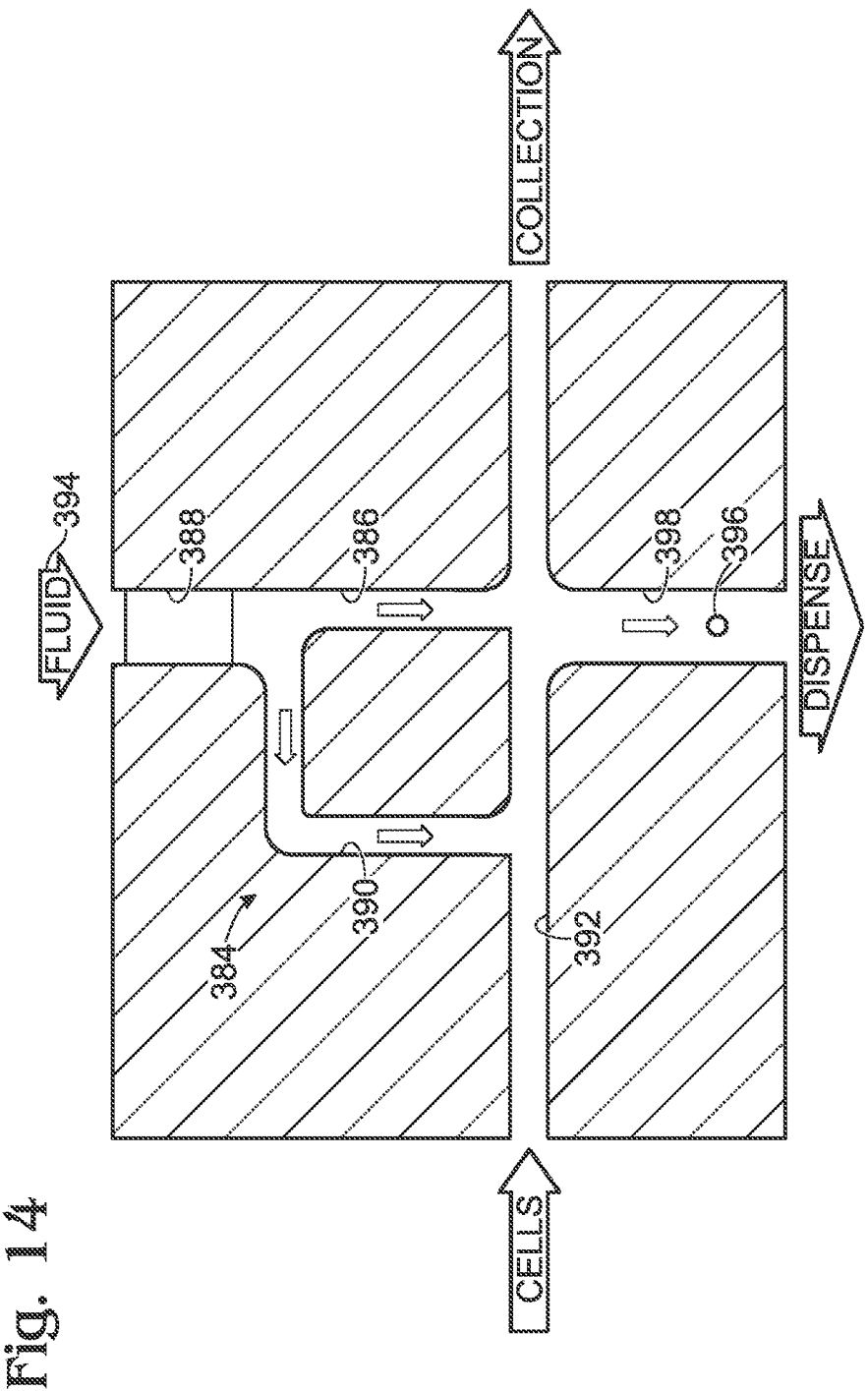

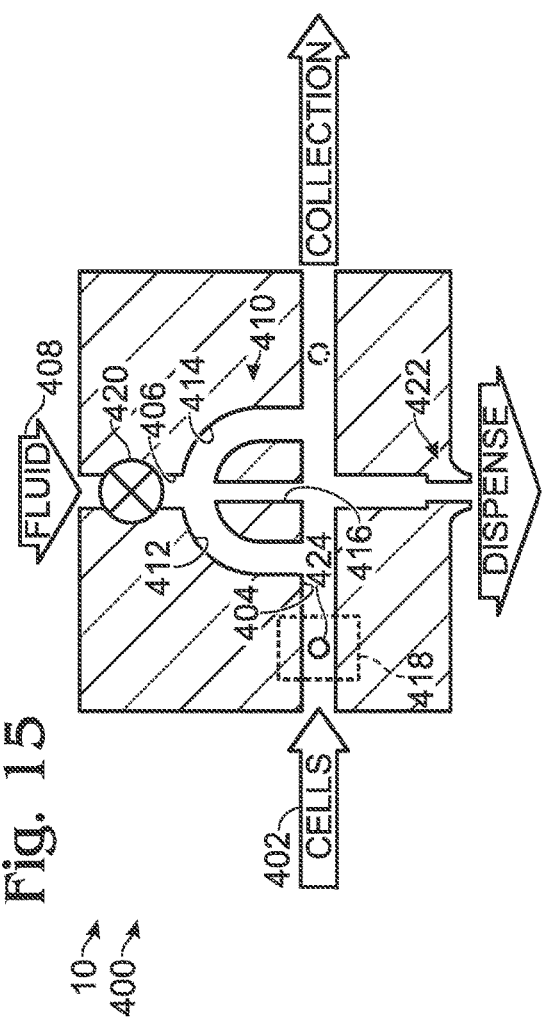

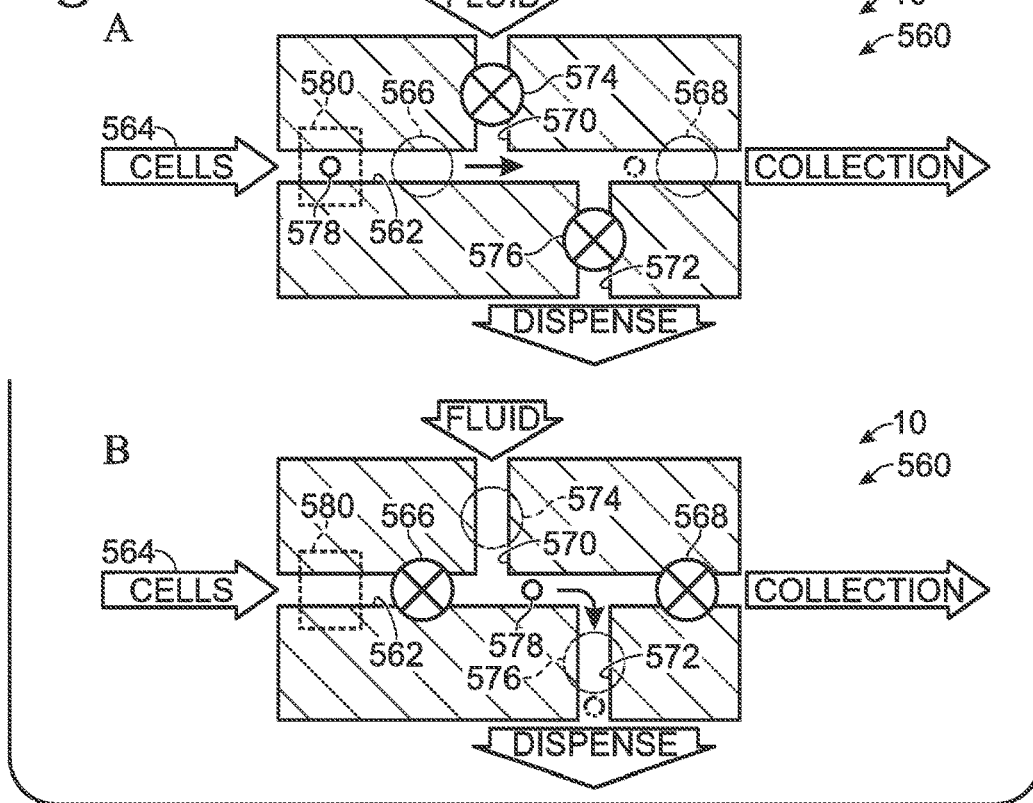
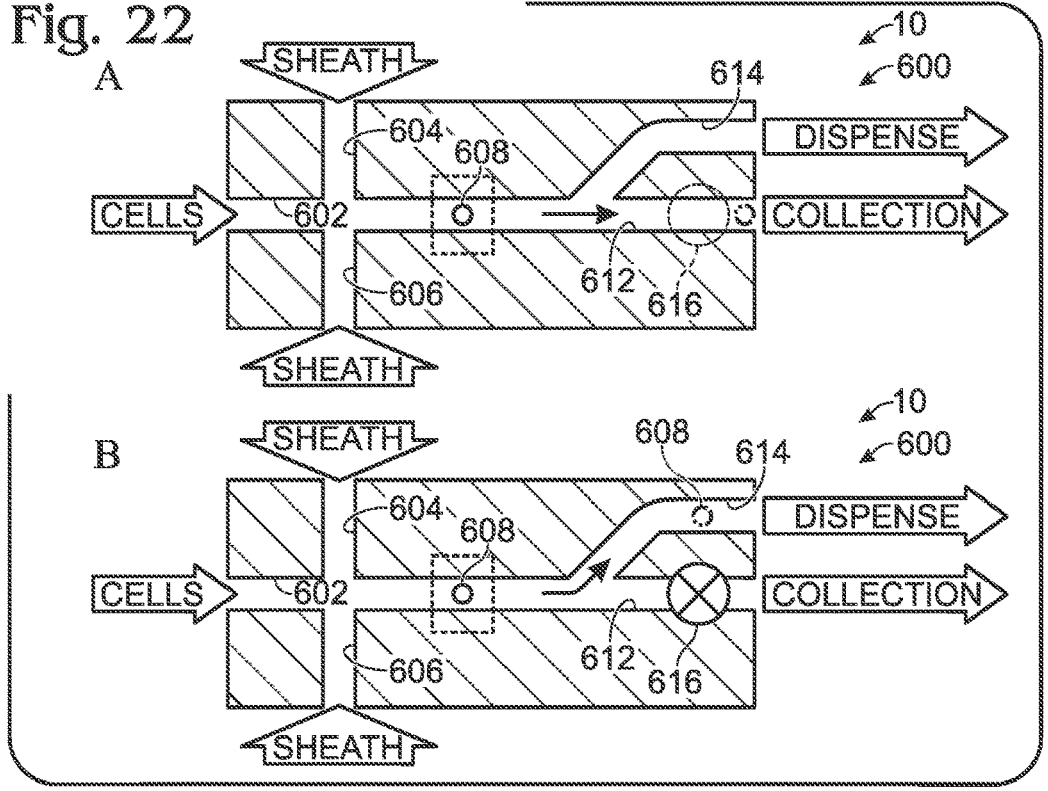

ON-DEMAND PARTICLE DISPENSING SYSTEM

CROSS-REFERENCES TO PRIORITY APPLICATIONS

This application is a continuation-in-part of U.S. patent application Ser. No. 14/479,132, filed Sep. 5, 2014, now U.S. Pat. No. 9,535,000; and U.S. patent application Ser. No. 14/479,155, filed Sep. 5, 2014.

U.S. patent application Ser. No. 14/479,132, in turn, is based upon and claims the benefit under 35 U.S.C. § 119(e) of the following U.S. provisional patent applications: Ser. No. 61/874,320, filed Sep. 5, 2013; and Ser. No. 61/902,664, filed Nov. 11, 2013.

U.S. patent application Ser. No. 14/479,155, in turn, is based upon and claims the benefit under 35 U.S.C. § 119(e) of the following U.S. provisional patent applications: Ser. No. 61/874,320, filed Sep. 5, 2013; and Ser. No. 61/902,664, filed Nov. 11, 2013.

Each of these priority applications is incorporated herein by reference in its entirety for all purposes.

INTRODUCTION

The ability to perform molecular and cellular analyses of biological systems has grown explosively over the past several decades. In particular, the advent and refinement of molecular and cellular techniques, such as DNA sequencing, gene cloning, monoclonal antibody production, cell transfection, amplification techniques (such as PCR), and transgenic animal formation, have fueled this explosive growth. These techniques have spawned an overwhelming number of identified genes, encoded proteins, engineered cell types, and assays for studying these genes, proteins, and cell types. Unfortunately, as the number of possible combinations of samples, reagents, and assays becomes nearly incalculable, it has become increasingly apparent that novel approaches are necessary even to begin to make sense of this complexity, especially within reasonable temporal and monetary limitations.

One approach to these difficulties has been to reduce the scale of assays, focusing on small volumes and small numbers of particles, including individual cells. The traditional method for dispensing a single cell (or other particle) for analysis is through dilution. Specifically, a solution containing the cells is diluted to a concentration such that each absorption/dispensing of pipette contains on average a single cell. However, this method is not accurate: aliquots may contain no cell, one cell, or multiple cells. Single cells also may be dispensed by pick-and-place robot systems, which locate an individual cell (for example, on a dish), pick up the cell, and place the cell at another location. However, pick-and-place systems need to locate each cell and require significant time if moving a substantial number of cells. Single cells also may be analyzed using flow cytometry, but this method is complex and expensive, and not set up for or intended to dispense single cells.

Thus, in view of these shortcomings, there is a need for systems that can effectively manipulate individual cells and other small particles, such as beads, in small volumes.

SUMMARY

The invention provides systems, including apparatus and methods, for the microfluidic manipulation, dispensing, and/or sorting of particles, such as cells and/or beads.

Features, functions, and advantages may be achieved independently in various embodiments of the present disclosure, or may be combined in yet other embodiments, further details of which can be seen with reference to the following description and drawings.

BRIEF DESCRIPTION OF THE DRAWINGS

FIG. 1 is a schematic diagram showing an illustrative on-demand cell dispensing system according to the present disclosure.

FIG. 2, Panels A-C, shows plan views of an illustrative diverter mechanism suitable for use in the system shown in FIG. 1, depicting three different positions of a sliding diverter.

FIG. 3 is a plan view of another illustrative diverter mechanism suitable for use in the system shown in FIG. 1, including a vacuum-actuated flexible membrane.

FIG. 4 is a sectional elevation view of the diverter mechanism of FIG. 3 taken at line 4-4.

FIG. 5 is a plan view of the diverter mechanism of FIG. 3 after actuation of the flexible membrane.

FIG. 6 is a sectional elevation view of the diverter mechanism of FIG. 5 taken at line 6-6.

FIG. 7 is a plan view of another illustrative diverter mechanism suitable for use in the system shown in FIG. 1, including a rotary paddle diverter.

FIG. 12, Panels A and B, shows plan views of another illustrative diverter mechanism suitable for use in the system shown in FIG. 1, including a branched dispensing fluid channel.

FIG. 13 is a plan view of an alternative embodiment of the diverter mechanism of FIG. 12.

FIG. 14 shows another illustrative diverter mechanism suitable for use in the system of FIG. 1, including two dispensing fluid branches.

FIG. 15 shows another illustrative diverter mechanism suitable for use in the system shown in FIG. 1, including a branched dispensing fluid channel having a central leg and a nozzle section formed at a dispensing area.

FIG. 16 shows another illustrative diverter mechanism suitable for use in the system shown in FIG. 1, including multiple sensing regions and multiple diverting areas.

FIG. 21, Panels A and B, shows another illustrative diverter mechanism suitable for use in the system shown in FIG. 1, including an offset-tee arrangement with four valves.

FIG. 22, Panels A and B, shows another illustrative diverter mechanism suitable for use in the system shown in FIG. 1, including a forking sample channel.

DETAILED DESCRIPTION

Figure 8:
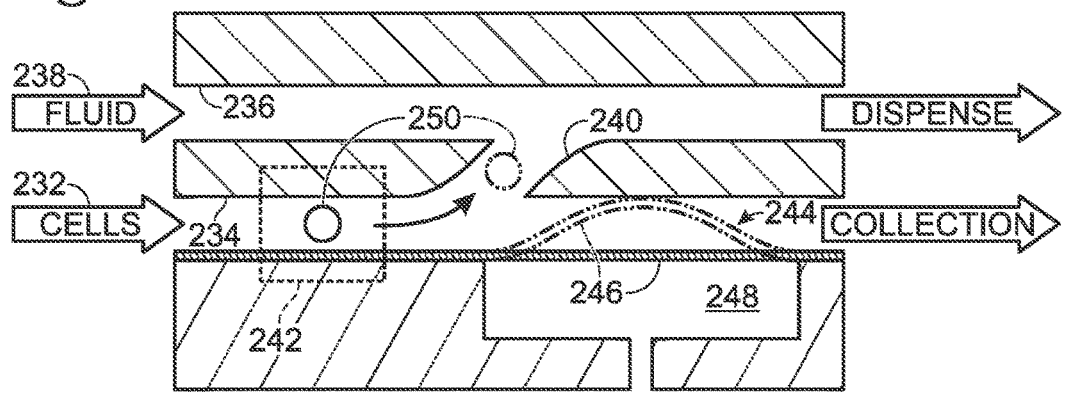
FIG. 8 is a plan view of another illustrative diverter mechanism suitable for use in the system shown in FIG. 1, including a pressure-actuated flexible membrane.

The invention provides systems, including apparatus and methods, for the microfluidic on-demand dispensing and/or sortation of particles, such as cells, viruses, organelles, beads, and/or vesicles. The invention also provides microfluidic mechanisms for carrying out the dispensing and sortation. These mechanisms may enable controlled input, movement/positioning, diversion, release, and/or output of particles. Furthermore, these mechanisms may be combined in any suitable order and/or employed for any suitable number of times within a system. Accordingly, these combinations may allow particles to be sorted or dispensed, among others, as single particles, mixed groups of particles, arrays of particles, heterogeneous particle sets, and/or homogeneous particle sets, among others, in series and/or in parallel. In addition, these combinations may enable microfluidic systems to be reused. Furthermore, these combinations may allow the dispensing of particles more efficiently, reliably, precisely, and/or with more viability than was previously possible.

Further aspects of the invention are described in the following sections: (I) overview of microfluidic systems, (II) physical structures of fluid networks, (III) particles, (IV) input mechanisms, (V) measurement and detection mechanisms, (VI) output mechanisms, (VII) overview of an on-demand dispensing system, and (VIII) examples.

I. OVERVIEW OF MICROFLUIDIC SYSTEMS

A. Definitions and Overview

Particle manipulations may be performed in microfluidic systems such as those described in this disclosure. A microfluidic system generally comprises any system in which very small volumes of fluid are stored and manipulated, generally less than about 500 µL, typically less than about 100 µL, and more typically less than about 10 µL. Microfluidic systems carry fluid in predefined paths through one or more microfluidic passages. A microfluidic passage may have a minimum dimension, generally height or width, of less than about 200, 100, or 50 µm. Passages are described in more detail below in Section II.

Microfluidic systems may include one or more sets of passages that interconnect to form a generally closed microfluidic network. Such a microfluidic network may include one, two, or more openings at network termini, or intermediate to the network, that interface with the external world. Such openings may receive, store, and/or dispense fluid. Dispensing fluid may be introduced directly into the microfluidic network or to sites external the microfluidic system. Such openings generally function in input and/or output mechanisms, described in more detail below, and may include reservoirs, also described in more detail below.

Microfluidic systems also may include any other suitable features or mechanisms that contribute to fluid and/or particle manipulation. For example, microfluidic systems may include regulatory or control mechanisms that determine aspects of fluid flow rate and/or path. Valves and/or pumps that may participate in such regulatory mechanisms are described in more detail below. Alternatively or additionally, microfluidic systems may include mechanisms that determine, regulate, and/or sense fluid temperature, fluid pressure, fluid flow rate, exposure to light, exposure to electric fields, magnetic field strength, and/or the like. Accordingly, microfluidic systems may include heaters, coolers, electrodes, lenses, gratings, light sources, pressure sensors, pressure transducers, microprocessors, microelectronics, and/or so on. Furthermore, each microfluidic system may include one or more features that act as a code to identify a given system. The features may include any detectable shape or symbol, or set of shapes or symbols, such as black-and-white or colored barcode, a word, a number, and/or the like, that has a distinctive position, identity, and/or other property (such as optical property).

B. Materials

Microfluidic systems may be formed of any suitable material or combination of suitable materials. Suitable materials may include elastomers, such as polydimethylsiloxane (PDMS); plastics, such as polystyrene, polypropylene, polycarbonate, etc.; glass; ceramics; sol-gels; silicon and/or other metalloids; metals or metal oxides; biological polymers, mixtures, and/or particles, such as proteins (gelatin, polylysine, serum albumin, collagen, etc.), nucleic acids, microorganisms, etc.; and/or the like.

C. Methods of Fabrication

Microfluidic systems, also referred to as chips, may have any suitable structure. Such systems may be fabricated as a unitary structure from a single component, or as a multi-component structure of two or more components. The two or more components may have any suitable relative spatial relationship and may be attached to one another by any suitable bonding mechanism.

In some embodiments, two or more of the components may be fabricated as relatively thin layers, which may be disposed face-to-face. The relatively thin layers may have distinct thickness, based on function. For example, the thickness of some layers may be about 10 to 250 µm, 20 to 200 µm, or about 50 to 150 µm, among others. Other layers may be substantially thicker, in some cases providing mechanical strength to the system. The thicknesses of such other layers may be about 0.25 to 2 cm, 0.4 to 1.5 cm, or 0.5 to 1 cm, among others. One or more additional layers may be a substantially planar layer that functions as a substrate layer, in some cases contributing a floor portion to some or all microfluidic passages.

Components of a microfluidic system may be fabricated by any suitable mechanism, based on the desired application for the system and on materials used in fabrication. For example, one or more components may be molded, stamped, and/or embossed using a suitable mold. Such a mold may be formed of any suitable material by micromachining, etching, soft lithography, material deposition, cutting, and/or punching, among others. Alternatively, or in addition, components of a microfluidic system may be fabricated without a mold by etching, micromachining, cutting, punching, and/or material deposition.

Microfluidic components may be fabricated separately, joined, and further modified as appropriate. For example, when fabricated as distinct layers, microfluidic components may be bonded, generally face-to-face. These separate components may be surface-treated, for example, with reactive chemicals to modify surface chemistry, with particle binding agents, with reagents to facilitate analysis, and/or so on. Such surface-treatment may be localized to discrete portions of the surface or may be relatively nonlocalized. In some embodiments, separate layers may be fabricated and then punched and/or cut to produce additional structure. Such punching and/or cutting may be performed before and/or after distinct components have been joined.

II. PHYSICAL STRUCTURES OF FLUID NETWORKS

A. Overview

Microfluidic systems may include any suitable structure(s) for the integrated manipulation of small volumes of fluid, including moving and/or storing fluid, and particles associated therewith. The structures may include passages, reservoirs, and/or regulators, among others.

1. Passages

Passages generally comprise any suitable path, channel, or duct through, over, or along which materials (e.g., fluid, particles, and/or reagents) may pass in a microfluidic system. Collectively, a set of fluidically communicating passages, generally in the form of channels, may be referred to as a microfluidic network. In some cases, passages may be described as having surfaces that form a floor, a roof, and walls. Passages may have any suitable dimensions and geometry, including width, height, length, and/or cross-sectional profile, among others, and may follow any suitable path, including linear, circular, and/or curvilinear, among others. Passages also may have any suitable surface contours, including recesses, protrusions, and/or apertures, and may have any suitable surface chemistry or permeability at any appropriate position within a channel. Suitable surface chemistry may include surface modification, by addition and/or treatment with a chemical and/or reagent, before, during, and/or after passage formation.

In some cases, passages, and particularly channels, may be described according to function. For example, passages may be described according to direction of material flow in a particular application, relationship to a particular reference structure, and/or type of material carried. Accordingly, passages may be inlet passages (or channels), which generally carry materials to a site, and outlet passages (or channels), which generally carry materials from a site. In addition, passages may be referred to as particle passages (or channels), reagent passages (or channels), focusing passages (or channels), perfusion passages (or channels), waste passages (or channels), and/or the like.

Passages may branch, join, and/or dead-end to form any suitable microfluidic network. Accordingly, passages may function in particle positioning, sorting, retention, treatment, detection, propagation, storage, mixing, and/or release, among others. Further aspects of passages are included throughout this Detailed Description.

2. Reservoirs

Reservoirs generally comprise any suitable receptacle or chamber for storing materials (e.g., fluid, particles and/or reagents), before, during, between, and/or after processing operations (e.g., measurement and/or treatment). Reservoirs, also referred to as wells, may include input, intermediate, and/or output reservoirs. Input reservoirs may store materials (e.g., fluid, particles, and/or reagents) prior to inputting the materials to a microfluidic network(s) portion of a chip. By contrast, intermediate reservoirs may store materials during and/or between processing operations. Finally, output reservoirs may store materials prior to outputting from the chip, for example, to an external processor or waste, or prior to disposal of the chip.

3. Regulators

Regulators generally comprise any suitable mechanism for generating and/or regulating movement of materials (e.g., fluid, particles, and/or reagents). Suitable regulators may include valves, pumps, and/or electrodes, among others. Regulators may operate by actively promoting flow and/or by restricting active or passive flow. Suitable functions mediated by regulators may include mixing, sorting, connection (or isolation) of fluidic networks, and/or the like.

III. PARTICLES

A. Overview

Microfluidic systems may be used to manipulate particles. A particle generally comprises any object that is small enough to be inputted and manipulated within a microfluidic network in association with fluid, but that is large enough to be distinguishable from the fluid. Particles, as used here, typically are microscopic or near-microscopic, and may have diameters of about 0.005 to 100 µm, 0.1 to 50 µm, or about 0.5 to 30 µm. Alternatively, or in addition, particles may have masses of about 10-20 to 10-5 grams, 10-16 to 10-7 grams, or 10-14 to 10-8 grams. Exemplary particles may include cells, viruses, organelles, beads, and/or vesicles, and aggregates thereof, such as dimers, trimers, etc.

B. Cells

1. Overview

Cells, as used here, generally comprise any self-replicating, membrane-bounded biological entity, or any nonreplicating, membrane-bounded descendant thereof. Nonreplicating descendants may be senescent cells, terminally differentiated cells, cell chimeras, serum-starved cells, infected cells, nonreplicating mutants, anucleate cells, etc.

Cells used as particles in microfluidic systems may have any suitable origin, genetic background, state of health, state of fixation, membrane permeability, pretreatment, and/or population purity, among others. Origin of cells may be eukaryotic, prokaryotic, archae, etc., and may be from animals, plants, fungi, protists, bacteria, and/or the like. Cells may be wild-type; natural, chemical, or viral mutants; engineered mutants (such as transgenics); and/or the like. In addition, cells may be growing, quiescent, senescent, transformed, and/or immortalized, among others, and cells may be fixed and/or unfixed. Living or dead, fixed or unfixed cells may have intact membranes, and/or permeabilized/disrupted membranes to allow uptake of ions, labels, dyes, ligands, etc., or to allow release of cell contents. Cells may have been pretreated before introduction into a microfluidic system by any suitable processing steps. Such processing steps may include modulator treatment, transfection (including infection, injection, particle bombardment, lipofection, coprecipitate transfection, etc.), processing with assay reagents, such as dyes or labels, and/or so on. Furthermore, cells may be a monoculture, generally derived as a clonal population from a single cell or a small set of very similar cells; may be presorted by any suitable mechanism such as affinity binding, FACS, drug selection, etc.; and/or may be a mixed or heterogeneous population of distinct cell types.

2. Eukaryotic Cells

Eukaryotic cells, that is, cells having one or more nuclei, or anucleate derivatives thereof, may be obtained from any suitable source, including primary cells, established cells, and/or patient samples. Such cells may be from any cell type or mixture of cell types, from any developmental stage, and/or from any genetic background. Furthermore, eukaryotic cells may be adherent and/or nonadherent. Such cells may be from any suitable eukaryotic organism including animals, plants, fungi, and/or protists.

Eukaryotic cells may be from animals, that is, vertebrates or invertebrates. Vertebrates may include mammals, that is, primates (such as humans, apes, monkeys, etc.) or nonprimates (such as cows, horses, sheep, pigs, dogs, cats, marsupials, rodents, and/or the like). Nonmammalian vertebrates may include birds, reptiles, fish, (such as trout, salmon, goldfish, zebrafish, etc.), and/or amphibians (such as frogs of the species *Xenopus*, Rana, etc.). Invertebrates may include arthropods (such as arachnids, insects (e.g., *Drosophila*), etc.), mollusks (such as clams, snails, etc.), annelids (such as earthworms, etc.), echinoderms (such as various starfish, among others), coelenterates (such as jellyfish, coral, etc.), porifera (sponges), platyhelminths (tapeworms), nemathelminths (flatworms), etc.

Eukaryotic cells may be from any suitable plant, such as monocotyledons, dicotyledons, gymnosperms, angiosperms, ferns, mosses, lichens, and/or algae, among others. Exemplary plants may include plant crops (such as rice, corn, wheat, rye, barley, potatoes, etc.), plants used in research (e.g., *Arabidopsis*, loblolly pine, etc.), plants of horticultural values (ornamental palms, roses, etc.), and/or the like.

Eukaryotic cells may be from any suitable fungi, including members of the phyla Chytridiomycota, Zygomycota, Ascomycota, Basidiomycota, Deuteromycetes, and/or yeasts. Exemplary fungi may include *Saccharomyces cerevisiae, Schizosaccharomyces pombe, Pichia pastoralis, Neurospora crassa*, mushrooms, puffballs, imperfect fungi, molds, and/or the like.

Eukaryotic cells may be from any suitable protists (protozoans), including amoebae, ciliates, *flagellates*, coccidia, microsporidia, and/or the like. Exemplary protists may include *Giardia lamblia, Entamoeba histolytica, Cryptosporidium*, and/or *N. fowleri*, among others.

Particles may include eukaryotic cells that are primary, that is, taken directly from an organism or nature, without subsequent extended culture in vitro. For example, the cells may be obtained from a patient sample, such as whole blood, packed cells, white blood cells, urine, sputum, feces, mucus, spinal fluid, tumors, diseased tissue, bone marrow, lymph, semen, pleural fluid, a prenatal sample, an aspirate, a biopsy, disaggregated tissue, epidermal cells, keratinocytes, endothelial cells, smooth muscle cells, skeletal muscle cells, neural cells, renal cells, prostate cells, liver cells, stem cells, osteoblasts, and/or the like. Similar samples may be manipulated and analyzed from human volunteers, selected members of the human population, forensic samples, animals, plants, and/or natural sources (water, soil, air, etc.), among others.

Alternatively, or in addition, particles may include established eukaryotic cells. Such cells may be immortalized and/or transformed by any suitable treatment, including viral infection, nucleic acid transfection, chemical treatment, extended passage and selection, radiation exposure, and/or the like. Such established cells may include various lineages such as neuroblasts, neurons, fibroblasts, myoblasts, myotubes, chondroblasts, chondrocytes, osteoblasts, osteocytes, cardiocytes, smooth muscle cells, epithelial cells, keratinocytes, kidney cells, liver cells, lymphocytes, granulocytes, and/or macrophages, among others. Exemplary established cell lines may include Rat-1, NIH 3T3, HEK 293, COS1, COS7, CV-1, C2C12, MDCK, PC12, SAOS, HeLa, Schneider cells, Junkat cells, SL2, and/or the like.

3. Prokaryotic Cells

Particles may be prokaryotic cells, that is, self-replicating, membrane-bounded microorganisms that lack membrane-bound organelles, or nonreplicating descendants thereof. Prokaryotic cells may be from any phyla, including Aquificae, Bacteroids, Chlorobia, Chrysogenetes, Cyanobacteria, Fibrobacter, Firmicutes, Flavobacteria, Fusobacteria, Proteobacteria, Sphingobacteria, Spirochaetes, Thermomicrobia, and/or Xenobacteria, among others. Such bacteria may be gram-negative, gram-positive, harmful, beneficial, and/or pathogenic. Exemplary prokaryotic cells may include *E. coli, S. typhimurium, B subtilis, S. aureus, C. perfringens, V. parahaemolyticus*, and/or *B. anthracis*, among others.

C. Viruses

Viruses may be manipulated as particles in microfluidic systems. Viruses generally comprise any microscopic/submicroscopic parasites of cells (animals, plants, fungi, protists, and/or bacteria) that include a protein and/or membrane coat and that are unable to replicate without a host cell. Viruses may include DNA viruses, RNA viruses, retroviruses, virions, viroids, prions, etc. Exemplary viruses may include HIV, RSV, rabies, hepatitis virus, Epstein-Barr virus, rhinoviruses, bacteriophages, prions that cause various diseases (CJD (Creutzfeld-Jacob disease, kuru, GSS (Gerstmann-Straussler-Scheinker syndrome), FFI (Fatal Familial Insomnia), Alpers syndrome, etc.), and/or the like.

D. Organelles

Organelles may be manipulated in microfluidic systems. Organelles generally comprise any particulate component of a cell. For example, organelles may include nuclei, Golgi apparatus, lysosomes, endosomes, mitochondria, peroxisomes, endoplasmic reticulum, phagosomes, vacuoles, chloroplasts, etc.

E. Beads

Beads may be manipulated in microfluidic systems. Beads generally comprise any suitable manufactured particles. Beads may be manufactured from inorganic materials, or materials that are synthesized chemically, enzymatically and/or biologically. Furthermore, beads may have any suitable porosity and may be formed as a solid or as a gel. Suitable bead compositions may include plastics (e.g., polystyrene), dextrans, glass, ceramics, sol-gels, elastomers, silicon, metals, and/or biopolymers (proteins, nucleic acids, etc.). Beads may have any suitable particle diameter or range of diameters. Accordingly, beads may be a substantially uniform population with a narrow range of diameters, or beads may be a heterogeneous population with a broad range of diameters, or two or more distinct diameters.

Beads may be associated with any suitable materials. The materials may include compounds, polymers, complexes, mixtures, phages, viruses, and/or cells, among others. For example, the beads may be associated with a member of a specific binding pair (see Section VI), such as a receptor, a ligand, a nucleic acid, a member of a compound library, and/or so on. Beads may be a mixture of distinct beads, in some cases carrying distinct materials. The distinct beads may differ in any suitable aspect(s), such as size, shape, an associated code, and/or material carried by the beads. In some embodiments, the aspect may identify the associated material. Codes are described further below.

F. Vesicles

Particles may be vesicles. Vesicles generally comprise any noncellularly derived particle that is defined by a lipid envelope. Vesicles may include any suitable components in their envelope or interior portions. Suitable components may include compounds, polymers, complexes, mixtures, aggregates, and/or particles, among others. Exemplary components may include proteins, peptides, small compounds, drug candidates, receptors, nucleic acids, ligands, and/or the like.

IV. INPUT MECHANISMS

A. Overview

Microfluidic systems may include one or more input mechanisms that interface with the microfluidic network(s). An input mechanism generally comprises any suitable mechanism for inputting material(s) (e.g., particles, fluid, and/or reagents) to a microfluidic network of a microfluidic chip, including selective (that is, component-by-component) and/or bulk mechanisms.

B. Internal/External Sources

The input mechanism may receive material from internal sources, that is, reservoirs that are included in a microfluidic chip, and/or external sources, that is, reservoirs that are separate from, or external to, the chip.

Input mechanisms that input materials from internal sources may use any suitable receptacle to store and dispense the materials. Suitable receptacles may include a void formed in the chip. Such voids may be directly accessible from outside the chip, for example, through a hole extending from fluidic communication with a fluid network to an external surface of the chip, such as the top surface. The receptacles may have a fluid capacity that is relatively large compared to the fluid capacity of the fluid network, so that they are not quickly exhausted. For example, the fluid capacity may be at least about 1, 5, 10, 25, 50, or 100 µL. Accordingly, materials may be dispensed into the receptacles using standard laboratory equipment, if desired, such as micropipettes, syringes, and the like.

Input mechanisms that input materials from external sources also may use any suitable receptacle and mechanism to store and dispense the materials. However, if the external sources input materials directly into the fluid network, the external sources may need to interface effectively with the fluid network, for example, using contact and/or noncontact dispensing mechanisms. Accordingly, input mechanisms from external sources may use capillaries or needles to direct fluid precisely into the fluid network. Alternatively, or in addition, input mechanisms from external sources may use a noncontact dispensing mechanism, such as "spitting," which may be comparable to the action of an inkjet printer. Furthermore, input mechanisms from external sources may use ballistic propulsion of particles, for example, as mediated by a gene gun.

C. Facilitating Mechanisms

The inputting of materials into the microfluidics system may be facilitated and/or regulated using any suitable facilitating mechanism. Such facilitating mechanisms may include gravity flow, for example, when an input reservoir has greater height of fluid than an output reservoir. Facilitating mechanisms also may include positive pressure to push materials into the fluidic network, such as mechanical or gas pressure, or centrifugal force; negative pressure at an output mechanism to draw fluid toward the output mechanism; and/or a positioning mechanism acting within the fluid network. The positioning mechanism may include a pump and/or an electrokinetic mechanism.

V. MEASUREMENT AND DETECTION MECHANISMS

A. Overview

Particles manipulated by a microfluidic system may be analyzed by one or more measurement mechanisms at one or more measurement sites. The measurement mechanisms generally comprise any suitable apparatus or method for detecting a preselected particle or particle characteristic (provided, for example, by the particle, a particle component, and/or an assay product, among others). The measurement sites generally comprise any suitable particle position or positions at which a measurement is performed, internal and/or external to the system.

B. Detection Methods

The measurement mechanism may employ any suitable detection method to analyze a sample, qualitatively and/or quantitatively. Suitable detection methods may include spectroscopic methods, electrical methods, hydrodynamic methods, imaging methods, and/or biological methods, among others, especially those adapted or adaptable to the analysis of particles. These methods may involve detection of single or multiple values, time-dependent or time-independent (e.g., steady-state or endpoint) values, and/or averaged or (temporally and/or spatially) distributed values, among others. These methods may measure and/or output analog and/or digital values.

Spectroscopic methods generally may include detection of any property of light (or a wavelike particle), particularly properties that are changed via interaction with a sample. Suitable spectroscopic methods may include absorption, luminescence (including photoluminescence, chemiluminescence, and electrochemiluminescence), magnetic resonance (including nuclear and electron spin resonance), scattering (including light scattering, electron scattering, and neutron scattering), diffraction, circular dichroism, and optical rotation, among others. Suitable photoluminescence methods may include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), fluorescence activated cell sorting (FACS), and their phosphorescence and other analogs, among others.

Electrical methods generally may include detection of any electrical parameter. Suitable electrical parameters may include current, voltage, resistance, impedance, capacitance, and/or power, among others.

Hydrodynamic methods generally may include detection of interactions between a particle (or a component or derivative thereof) and its neighbors (e.g., other particles), the solvent (including any matrix), and/or the microfluidic system, among others, and may be used to characterize molecular size and/or shape, or to separate a sample into its components. Suitable hydrodynamic methods may include chromatography, sedimentation, viscometry, and electrophoresis, among others.

Imaging methods generally may include detection of spatially distributed signals, typically for visualizing a sample or its components, including optical microscopy and electron microscopy, among others.

Biological methods generally may include detection of some biological activity that is conducted, mediated, and/or influenced by the particle, typically using another method, as described above.

C. Detection Sites

The measurement mechanism may be used to detect particles and/or particle characteristics at any suitable detection site, internal and/or external to the microfluidic system.

Suitable internal detection sites may include any site(s) in or on a microfluidic system (a chip). These sites may include channels, chambers, and/or traps, and portions thereof, and may be referred to herein as sensing regions. Particles or particle characteristics may be detected while the particles (or released components/assay products) are stationary or moving. Stationary particles may be encountered following particle retention, for example, cells growing in a cell chamber. Moving particles may be encountered before and/or after particle retention, or upon confinement to a region. In particular, particles may be moved past a detection site by any suitable positioning mechanism, for example, by fluid flow (flow-based detection).

D. Detected Characteristics

The measurement method may detect and/or monitor any suitable characteristic of a particle, directly and/or indirectly (e.g., via a reporter molecule). Suitable characteristics may include particle identity, number, concentration, position (absolute or relative), composition, structure, sequence, and/or activity among others. The detected characteristics may include molecular or supramolecular characteristics, such as the presence/absence, concentration, localization, structure/modification, conformation, morphology, activity, number, and/or movement of DNA, RNA, protein, enzyme, lipid, carbohydrate, ions, metabolites, organelles, added reagent (binding), and/or complexes thereof, among others. The detected characteristics also may include cellular characteristics, such as any suitable cellular genotype or phenotype, including morphology, growth, apoptosis, necrosis, lysis, alive/dead, position in the cell cycle, activity of a signaling pathway, differentiation, transcriptional activity, substrate attachment, cell-cell interaction, translational activity, replication activity, transformation, heat shock response, motility, spreading, membrane integrity, and/or neurite outgrowth, among others.

VI. OUTPUT MECHANISMS

Microfluidic systems may include one or more output mechanisms that interface with the microfluidic network(s). An output mechanism generally comprises any suitable mechanism for outputting material(s) (e.g., fluid, particles, and/or reagents) from a microfluidic system, or portions thereof, including selective and/or bulk mechanisms. The output mechanism may direct outputted material to any suitable location, such as an internal and/or external sink. A sink generally comprises any receptacle or other site for receiving outputted materials, for disposal (e.g., a waste site) or for further study or manipulation (e.g., a collection site). The outputting of materials from the microfluidics system may be facilitated and/or regulated using any suitable facilitating mechanism, such as sources of internal pressure and/or external vacuum. The output mechanism may include a selection mechanism, such as a filter, that selects outputted materials based on some criterion, such as whether the material is a particle or a fluid.

VII. DESCRIPTION OF AN ON-DEMAND CELL DISPENSING SYSTEM

This disclosure describes microfluidic methods and systems for on-demand dispensing of particles such as those described in Section III above. The terms "particle" and "cell" are used interchangeably herein to indicate any such object.

FIG. 1 shows a schematic view of an illustrative on-demand cell dispensing system 10. In some examples, system 10 may include a microfluidic chip configured to detect particles moving in a channel and to selectively dispense one or more of the detected particles, for example, onto a substrate or into a target vessel. In some examples, the microfluidic chip may be placeable into an instrument and may be disposable following use. The microfluidic chip may be configured to engage with a manifold in the instrument to establish fluidic connections and provide a source of liquid to the chip and system.

System 10 may include a cell passage or channel 12 configured to direct a moving and/or pressurized solution 14 containing one or more particles. Channel 12, and other channels discussed herein, may include any suitable structure configured as a microfluidic pathway for conducting a fluid, and may be any suitable shape or size as described above in Section II. Solution 14 may include particles in a buffer or other liquid, and may be hydrodynamically focused, such as by using a sheath fluid.

System 10 may include a sensing region 16 configured to detect the presence of a particle of interest in channel 12 and to communicate that detection information to a controller 18. Sensing region 16 may include any suitable detector and/or sensor configured to detect the presence of a particle meeting certain selected criteria. For example, sensing region 16 may include optical, electrical, electromagnetic, and/or chemical detectors. Various detection methods may be used, independently or in combination, such as forward- or side-scatter signals, impedance measurements (e.g., Coulter counters), ferrous particles, photomultiplier tube (PMT), and/or fluorescence activated cell sorting (FACS), and/or any other suitable detection and measuring method described above in Section V.

System 10 may include one or more sensing regions 16. For example, sensing regions may be arranged in series to detect particles not previously detected and removed from channel 12 or arranged in parallel to detect particles in multiple branches of channel 12. In some examples, additional sensing regions may be included in a destination channel or other suitable location to provide verification of expected particle relocation.

Controller 18 may include any suitable electronic controller configured to receive detection information from sensing region 16 and take selected actions in response to the information received. For example, controller 18 may include a microprocessor and a digital memory configured to store instructions carried out by the microprocessor in response to certain inputs. In some examples, controller 18 may respond to an input from sensing region 16 indicating that a particle meeting predetermined criteria has been detected. Controller 18 may then initiate an output signal causing actuation of a diverter mechanism 20.

Diverter mechanism 20 may include any suitable device configured to move the detected particle from channel 12 into a dispensing channel 22, which may contain or selectively contain a pressurized dispensing fluid 24. Diverter mechanism 20 may include one or more active or passive mechanical components, motors, hydraulics, pneumatics, pressurized fluidics, vacuum generators, electrical or magnetic fields, thermal expansion and/or contraction, piezo-electric components, and the like. In some examples, diverter mechanism 20 may physically redirect a bulk of solution containing the particle. In some examples, diverter mechanism 20 may urge the particle into dispensing channel 22 through an interconnecting pathway. In some examples, diverter mechanism 20 may utilize valves or other suitable devices to control dispensing fluid 24, which may be used to confine, flush, and/or carry the particle into or through dispensing channel 22.

Undiverted particles and solution 14 may continue to a waste collection area 26, while diverted particles, solution 14, and/or dispensing fluid 24 may be directed to a dispensing area 28. Waste collection area 26 may include a collection device such as a vial or container, or may be redirected to an input of channel 12 for additional particle diversion, or elsewhere for additional processing. Cell solution 14 may be reused as appropriate.

The diverter mechanism of system 10 may divert a bulk of liquid surrounding the particle of interest into a dispensing area, for example, via a nozzle. This may facilitate a reduction in adverse effects due to manufacturing or operational tolerances on dispensing efficiency. Moreover, in this manner a dispensed cell or particle is kept in an aqueous environment, which may be critical to maintaining its health and/or structural integrity.

Dispensing area 28 may include any suitable location where a user wishes the particle or particles to be dispensed. For example, dispensing area 28 may include one or more locations on a substrate, or a target vessel. Moreover, system 10 may include multiple diverter mechanisms 20 and/or dispensing channels 22. Accordingly, system 10 may be configured as a sorting device in which cells are diverted and dispensed according to their sensed characteristics.

System 10 may be mounted on a stable frame, preventing vibration which may affect performance. In some examples, a vessel such as a micro-well plate may be placed under a dispensing nozzle, so that dispensed liquid as well as particles rests at the bottom of the plate wells. The vessel may be placed on an X-Y stage in order to control the position of the wells with respect to the dispensing nozzle. Dispensing of multiple particles into the same position may be achieved by maintaining the substrate/vessel in place. The system preferably includes mounting features, such as holes or apertures, allowing it to be easily positioned in a dedicated instrument. An assembled system may include a microfluidic chip which is sealed by means of a laminate and a manifold on which a valve is mounted. Generally, the manifold assembly is a permanent piece and the chip assembly may be either disposable or washable. The manifold may contain a valve for providing pressurized liquid to the chip on demand. In order to provide the required liquid or buffers to the chip, the manifold assembly may engage with the chip and seal by means such as O-rings, a flexible gasket, and/or surface-to-surface contact.

VIII. EXAMPLES

This section describes selected aspects and embodiments of the present disclosure related to on-demand cell dispensing devices. These examples are intended for illustration only and should not limit or define the entire scope of the present disclosure. The features disclosed in this section may be combined with each other and with features disclosed in other sections.

Example 1. Parallel Channel Slide Diverter

This example describes a parallel channel sliding diverter suitable for use in an on-demand cell dispensing system 10 according to the present disclosure; see FIG. 2.

FIG. 2 shows three successive overhead views of an exemplary diverter mechanism 100 for use in system 10. In this example, a cell sample channel 102 containing a solution of sample cells 104 is arranged substantially parallel to a dispensing channel 106 containing a pressurized dispensing fluid 108. The respective liquids generally flow in the same direction as indicated by the arrows in the drawings. A multi-aperture slide diverter 110 is disposed transverse to the two channels 102 and 106 such that a first aperture 112 is normally in line with sample channel 102 and a second aperture 114 is normally in line with dispensing channel 106, as shown in Panel A of FIG. 2. A sensing region 116 is positioned adjacent to or within sample channel 102, upstream of diverter 110.

A sensor in sensing region 116 may be configured to signal the controller (not shown) when a particle of interest 118 is detected. In response to the sensed particle of interest, the controller then repositions diverter 110 as shown in Panels B and C of FIG. 2, by causing the diverter to travel along diverter way 120 such that, in the position shown in Panel C of FIG. 2, aperture 112 aligns with dispensing channel 106 rather than sample channel 102.

Depending on the distance between the sensing region and aperture 112, as well as other factors such as expected or measured particle speed, the controller repositions diverter 108 when particle of interest 118 is expected to be within aperture 112. Accordingly, repositioning the diverter causes particle 118 and a bulk of surrounding liquid 122 to be placed into the flow of dispensing channel 106.

After a delay sufficient to allow particle 118 to be carried out of aperture 112 by the flow of dispensing fluid 108, diverter 110 is repositioned back to the original position, aligning aperture 112 with sample channel 102 and aperture 114 with dispensing channel 106. This action may be initiated, for example, by the controller, or may be caused by a delay built into the diverter or an actuating mechanism of the diverter. The actuating mechanism in this example may include one or more electromagnets controllable by the controller for urging diverter 110 along way 120.

Diverter 110 may include one or more additional apertures. For example, a third aperture (not shown) may be configured to align with sample channel 102 when diverter 110 is in the position shown in Panel C of FIG. 2. This additional aperture would allow solution 104 in sample channel 102 to continue flowing while particle 118 is being diverted. This may be desirable, for example, if multiple slide diverters are arranged in series, to continue selecting or sorting additional particles while particle 118 is diverted.

In some embodiments of this example, one or more additional sensing regions may be included. For example, an additional sensing region may be included for verifying that particle 118 was in fact present in aperture 112, and/or that particle 118 passed into dispensing channel 106 following diversion.

Example 2. Parallel Channel Vacuum Diverter

This example describes a parallel channel vacuum diverter suitable for use in an on-demand cell dispensing system 10 according to the present disclosure; see FIGS. 3-6.

FIGS. 3-6 show an exemplary diverter mechanism 140 for use in system 10. FIG. 3 shows a plan view of diverter 140 in a normal operating mode 142, and FIG. 4 shows a sectional side view taken along line 4-4 with the mechanism in the same position. FIGS. 5 and 6, respectively, show corresponding views of diverter 140 in a particle-diverting mode 144.

In this example, a cell-containing solution 146 flows through a sample channel 148 arranged substantially parallel to a dispensing channel 150 containing a pressurized dispensing fluid 152. The respective liquids generally flow in the same direction as indicated by the arrows in the drawings. A connecting channel 154 fluidly connects sample channel 148 to dispensing channel 150. A sensing region 156 is disposed in sample channel 148 upstream of the connection between channel 148 and channel 154. In the example shown in the drawings, connecting channel 154 is substantially perpendicular to channels 148 and 150. However, other transverse orientations may be suitable.

Mechanism 140 includes a flexible membrane 158 covering an underlying vacuum chamber 160 in dispensing channel 150 near the junction of channel 150 and connecting channel 154. During normal operation, membrane 158 conforms to and forms a part of the wall of channel 150 as indicated in FIGS. 3 and 4. Relative operating pressures in the respective channels keep cell solution 146 from entering dispensing channel 150.

As shown in FIGS. 5 and 6, when a particle of interest 162 is detected in sensing region 156, the controller responds by drawing a vacuum in vacuum chamber 160, causing flexible membrane 158 to deform. This deformation causes a drop in pressure in the region of membrane 158 below the operating pressure of cell solution 146, resulting in a pressure differential across the length of connecting channel 154. Accordingly, particle 162 is drawn across the connecting channel into the flow of the dispensing channel.

After a suitable time has passed, or in response to a confirmation signal indicating a successful diversion of the particle, the controller releases the vacuum in chamber 160, causing membrane 158 to return to the normal operating position of mode 142. This in turn causes pressures to return to normal, if they have not yet equilibrated, and prepares the diverter for the next particle to be diverted.

Example 3. Parallel Channel Paddle Diverter

This example describes a parallel channel paddle diverter suitable for use in an on-demand cell dispensing system 10 according to the present disclosure; see FIG. 7.

FIG. 7 shows an exemplary diverter mechanism 200 for use in system 10 in a plan view. In this example, a cell-containing solution 202 flows through a sample channel 204 arranged substantially parallel to a dispensing channel 206 containing a dispensing fluid 208. The respective liquids generally flow in the same direction as indicated by the arrows in the drawings. A connecting channel 210 selectively connects sample channel 204 to dispensing channel 206 depending on the position of a rotary paddle 212. A sensing region 214 is disposed in sample channel 204 upstream of the connection between channel 204 and channel 210.

When a particle of interest 216 is detected in sensing region 214, the controller responds by repositioning paddle 212 from its original position shown in solid lines to a diverting position shown in phantom lines in FIG. 7. This diverting position directs the flow from sample channel 204 across channel 210 and into dispensing channel 206. Pressures and flow rates may be controlled such that dispensing fluid 208 does not resist the entry of the particle and solution into the dispensing channel.

After a suitable amount of time, paddle 212 may be repositioned to its original state to reset diverter 200 for a subsequent diversion event. In some examples, a second sensing region may be disposed downstream of the diverter in dispensing channel 206 to confirm that the particle was indeed diverted successfully. In some examples, this confirmation may be a signal to the controller indicating that the paddle may be safely reset.

Example 4. Parallel Channel Blocking Diverter

This example describes a parallel channel blocking diverter suitable for use in an on-demand cell dispensing system 10 according to the present disclosure; see FIG. 8.

FIG. 8 shows an exemplary diverter mechanism 230 for use in system 10 in a plan view. In this example, a cell-containing solution 232 flows through a sample channel 234 arranged substantially parallel to a dispensing channel 236 containing a dispensing fluid 238. The respective liquids generally flow in the same direction as indicated by the arrows in the drawings. A connecting channel 240 connects sample channel 234 to dispensing channel 236. A sensing region 242 is disposed in sample channel 234 upstream of the connection between channel 234 and channel 240.

A blocking device 244 is disposed adjacent to sample channel 234 downstream of the connection between channel 234 and connecting channel 240. In this example, blocking device 244 includes a flexible membrane 246 and a pressure chamber 248. However, blocking device 244 may include other mechanisms, such as a sliding block or a valve, and in general may include any suitable device configured to selectively block or restrict flow in channel 234.

When a particle of interest 250 is detected in sensing region 242, the controller responds by pressurizing chamber 248, causing membrane 246 to flex into channel 234 as shown in phantom lines in FIG. 8, thereby blocking flow in the channel. With the sample channel blocked, the flow of solution including particle 250 is directed from sample channel 234 across connecting channel 240 and into dispensing channel 236. Pressures and flow rates may be controlled such that dispensing fluid 238 does not resist the entry of the particle and solution into the dispensing channel.

After a suitable amount of time, or in response to a confirmation that diversion was successful, chamber 248 may be depressurized to reset diverter 230 for a subsequent diversion event. As in some other examples described above, a second sensing region may be disposed downstream of the diverter in dispensing channel 236 to confirm that the particle was indeed diverted successfully.

Example 5. Parallel Channel DEP Diverter

Figure 9:
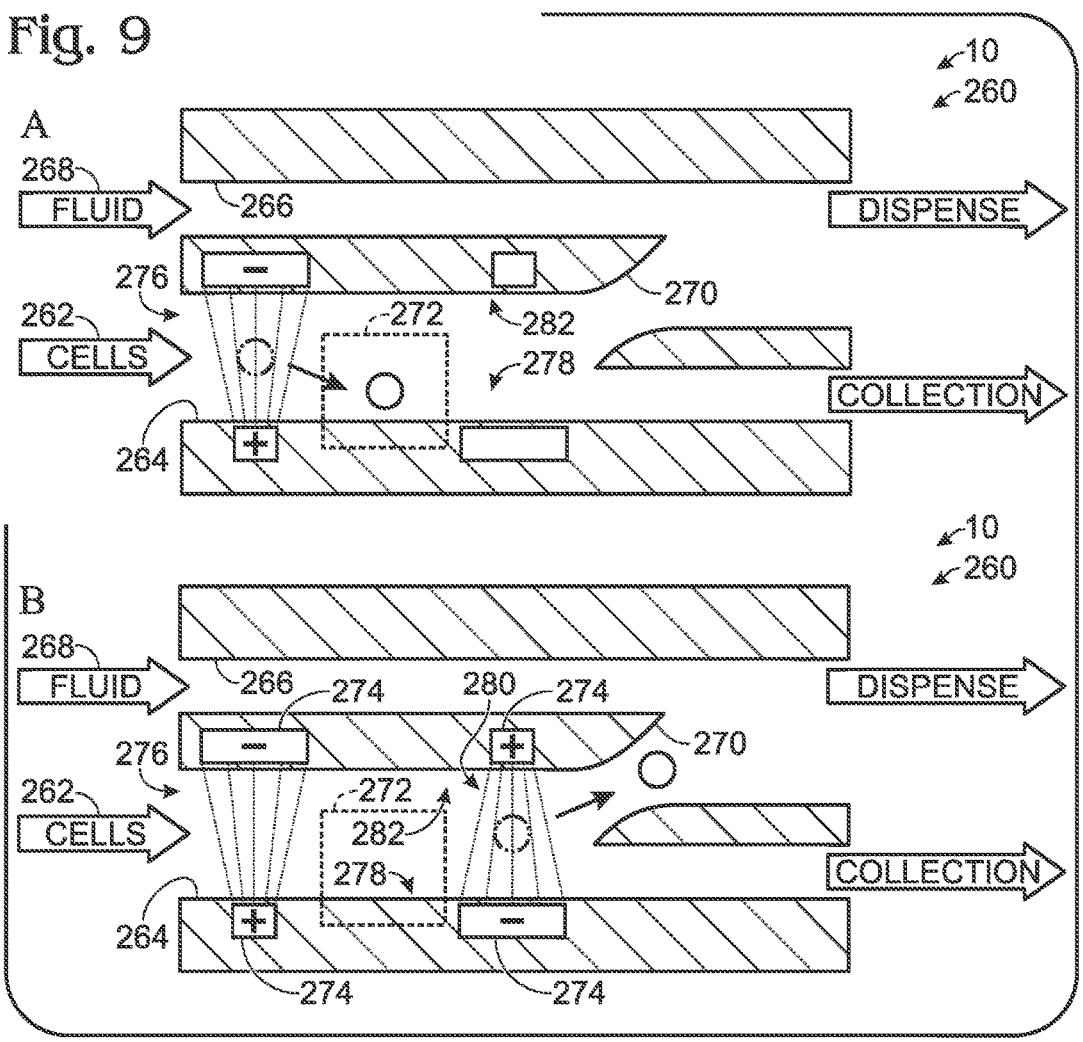
FIG. 9, Panels A and B, show a plan view of another illustrative diverter mechanism suitable for use in the system shown in FIG. 1, including a dielectrophoresis (DEP) diverter and showing two states of the diverter.

This example describes a parallel channel dielectrophoresis (DEP) diverter suitable for use in an on-demand cell dispensing system 10 according to the present disclosure; see FIG. 9.

FIG. 9 shows an exemplary diverter mechanism 260 for use in system 10 in a plan view. In this example, a cell-containing solution 262 flows through a sample channel 264 arranged substantially parallel to a dispensing channel 266 containing a dispensing fluid 268. The respective liquids generally flow in the same direction as indicated by the arrows in the drawings. A connecting channel 270 connects sample channel 264 to dispensing channel 266. A sensing region 272 is disposed in sample channel 264 upstream of the connection between channel 264 and channel 270.

In this example, rather than redirecting flow, the diverter mechanism urges particles in desired directions using DEP. Multiple electrodes 274 adjacent to sample channel 264 are configured to create non-uniform electrical fields across the channel. Because of the DEP effect, these fields will exert a net force on a neutral body such as a cell, causing the body to move transversely within the channel. Accordingly, the electrodes are configured to generate a first field 276 such that all passing particles are moved to a near side 278 of the sample channel as shown in Panel A of FIG. 9. When a particle of interest is detected in sensing region 272, the controller causes a temporary second field 280 to be generated, thereby moving that particle to an opposite side 282 of the channel, as shown in Panel B of FIG. 9. Channels 264, 266, and 270 are configured such that particles on opposite side 282 of the channel are directed through the connecting channel and into the dispensing channel, while particles on near side 278 continue through the sample channel to the waste collection area.

Example 6. Cross Channel Valved Diverter

Figure 10:
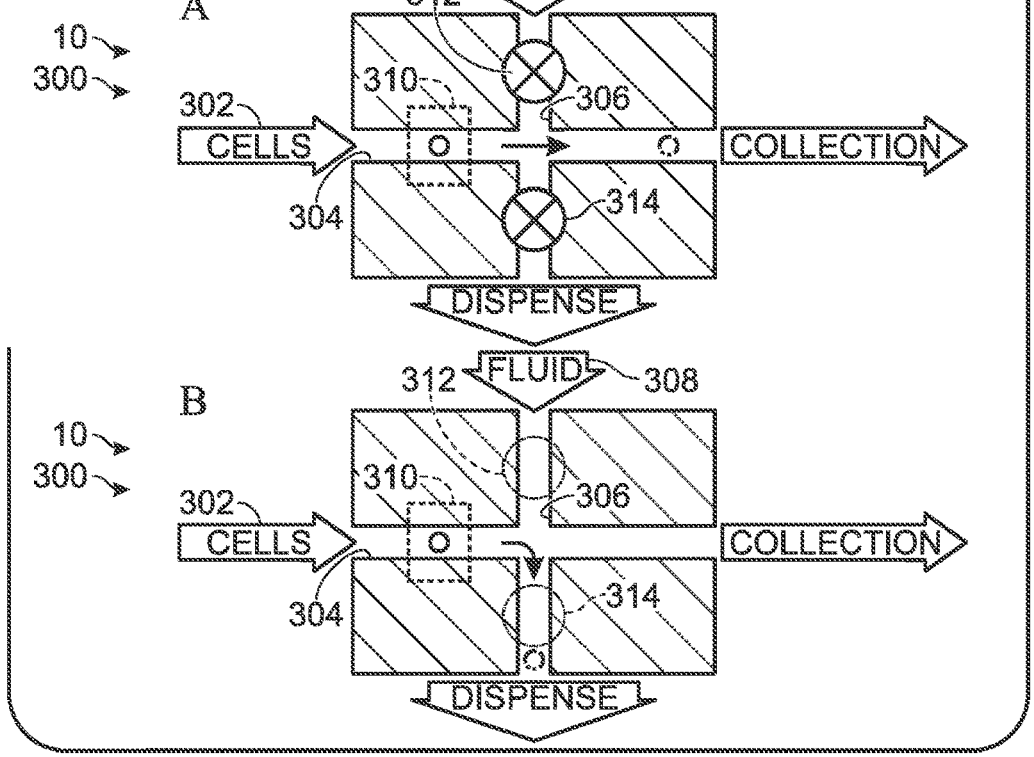
FIG. 10, Panels A and B, shows plan views of another illustrative diverter mechanism suitable for use in the system shown in FIG. 1, including a crossed-channel valved diverter and showing the valves in a non-diverting and a diverting state.

This example describes a crossed-channel valved diverter suitable for use in an on-demand cell dispensing system 10 according to the present disclosure; see FIG. 10.

FIG. 10 shows an exemplary diverter mechanism 300 for use in system 10 in an overhead plan view. In this example, a cell-containing solution 302 flows through a sample channel 304 arranged transverse to a dispensing channel 306. Dispensing channel 306 contains a dispensing fluid 308 pressurized to a greater pressure than solution 302. The respective liquids are configured to generally flow in transverse directions as indicated by the arrows in the drawings. A sensing region 310 is disposed in sample channel 304 upstream of the connection between channel 304 and channel 306. In normal operation, solution 302 is prevented from interacting with fluid 308 by one or more valves such as inlet valve 312 and outlet valve 314. Valves 312 and 314 are normally closed, as indicated by the solid circles containing an "X" in Panel A of FIG. 10. Open valves are indicated by an open phantom circle. This valve position convention is used throughout the drawings.

When a particle of interest 316 is detected in sensing region 310, the controller opens valves 312 and 314, as shown in phantom lines in Panel B of FIG. 10. Opening these valves causes the higher pressure dispensing fluid to reach the junction between the two channels while particle 316 is present, thereby diverting the particle down the dispensing channel. After a suitable amount of time, and/or upon confirmation that particle 316 has been successfully diverted, valves 312 and 314 are closed to reset the system for a subsequent diversion event.

Example 7. Cross Channel Rotary Diverter

Figure 11:
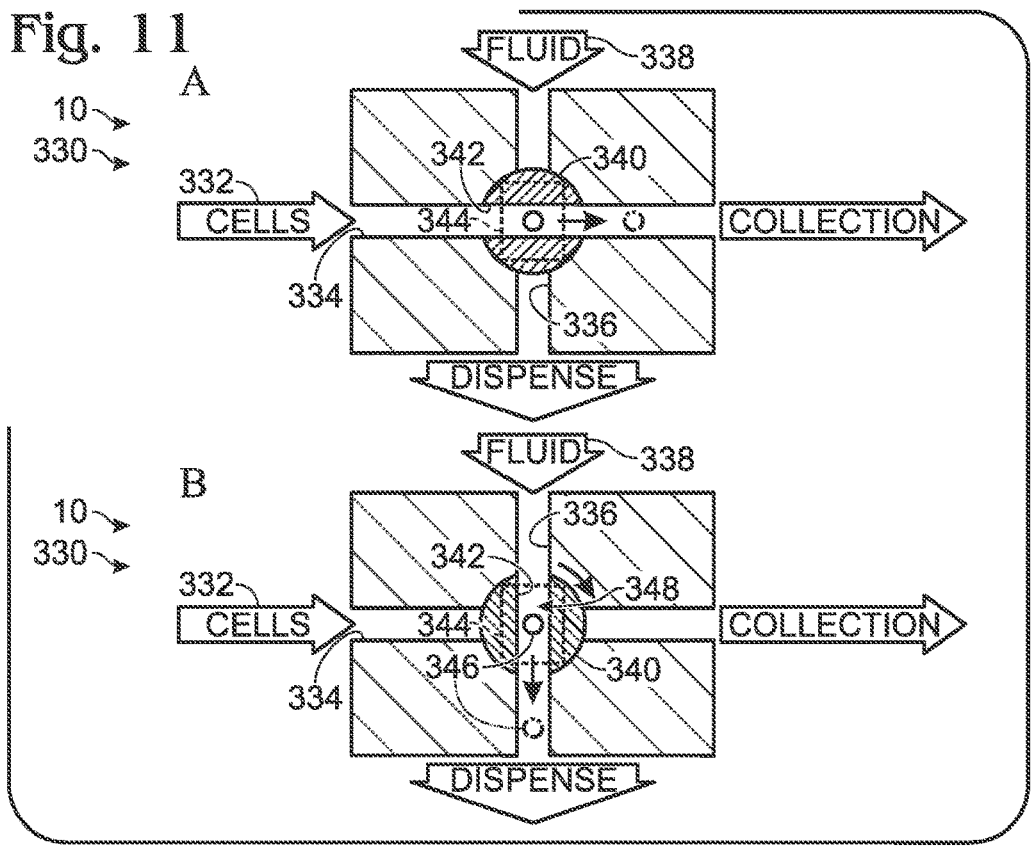
FIG. 11, Panels A and B, shows plan views of another illustrative diverter mechanism suitable for use in the system shown in FIG. 1, including a rotary diverter configured to selectively connect channels and showing a non-diverting and a diverting state of the diverter.

This example describes a crossed-channel rotary diverter suitable for use in an on-demand cell dispensing system 10 according to the present disclosure; see FIG. 11.

FIG. 11 shows an exemplary diverter mechanism 330 for use in system 10 in an overhead plan view. In this example, a cell-containing solution 332 flows through a sample channel 334 arranged transverse to a dispensing channel 336. Dispensing channel 336 contains a dispensing fluid 338 pressurized to a greater pressure than solution 332. The respective liquids are configured to generally flow in transverse directions as indicated by the arrows in the drawings.

Diverter 330 includes a rotary diverter 340 located at the junction of channels 334 and 336 such that the rotary diverter is in the path of both channels, and separates each channel into two discrete sections. A diverter channel 342 of the rotary diverter selectively connects the respective sections of either channel 334 or channel 336, depending on the rotational position of rotary diverter 340.

A sensing region 344 may be disposed at any suitable location sufficient to detect a particle of interest 346 and allow rotary diverter 340 to divert the particle by rotating. In some examples, sensing region 344 may be located upstream of the rotary diverter. In this example, sensing region 344 is located at the rotary diverter, and the system is configured to be capable of diverting particle 346 after the particle is detected within diverter channel 342.

In normal operation, rotary diverter 340 is oriented such that diverter channel 342 is aligned with and connects the sections of sample channel 334 as shown in Panel A of FIG. 11. Solution 332 and particles that do not meet the preselected criteria are passed through channel 342 to the collection area. When a particle of interest such as particle 346 is detected in sensing region 344, the controller causes an actuator to reposition the rotary diverter to align diverter channel 342 with the sections of dispensing channel 336 as shown in Panel B of FIG. 11. This action causes a bulk of solution 348, along with particle 346, to be placed in line with the flow of dispensing fluid 338 and carried to the dispensing area.

After a suitable time or upon confirmation that particle 346 has been successfully diverted, the controller causes the actuator to reposition rotary diverter 340 to again align diverter channel 342 with sample channel 334 in preparation for a subsequent diversion event.

Example 8. Cross Multi-channel Pressure Diverter and Dispensing Nozzle

This example describes various crossed multi-channel diverters suitable for use in an on-demand cell dispensing system 10 according to the present disclosure; see FIGS. 12-18.

FIG. 12 shows an exemplary diverter mechanism 360 for use in system 10 in an overhead plan view. In this example, a cell-containing solution 362 flows through a sample channel 364 arranged transverse to a dispensing channel 366. Solution 362 may be pressurized in a typical range from about 0.1 to about 1 psi, depending on desired flow rate. Other pressures may also be suitable. Dispensing channel 366 contains a dispensing fluid 368 pressurized to a greater pressure than solution 362. Typically, the pressure of the dispensing fluid may be from about 1 to about 5 psi. Dispensing channel 366 also includes a branched section 370 in which channel 366 forks into two symmetrical channels 372 and 374, both of which are connected to sample channel 364. The respective liquids are configured to generally flow in the transverse directions as indicated by the arrows in the drawings.

A sensing region 376 is disposed in sample channel 364 upstream of the connection between branched section 370 and channel 364. In normal operation, fluid 368 is prevented from interacting with solution 362 by one or more valves such as inlet valve 378 and outlet valve 380. In other examples, channels 372' and 374' in branched section 370' may each include a branch inlet valve 381, as shown in diverter mechanism 360' of FIG. 13. Valves 378 and 380 are normally closed, as indicated in Panel A of FIG. 12.

In normal operation, flow proceeds down sample channel 364, and solution 362 is directed to the collection area along with any particles that do not meet predetermined criteria. When a particle of interest 382 is detected in sensing region 376, the controller responds by opening valves 378 and 380, releasing the pressurized fluid in dispensing channel 366 as shown in Panel B of FIG. 12. Because channels 372 and 374 in branched section 370 are symmetrical, a substantially equivalent flow passes through each of the branches, entering sample channel 364 on opposite sides of particle 382. This effectively confines particle 382 and then flushes it down dispensing channel 366 through outlet valve 380. The overall width of branched section 370 is configured to minimize the effect of typical manufacturing variation in channel dimensions and other tolerance issues on confining efficiency.

After a suitable time or upon confirmation that particle 382 has been successfully diverted, the controller closes the inlet and outlet valves in preparation for a subsequent diversion event.

FIG. 14 shows another embodiment of a branched diverter mechanism similar to diverter mechanism 360. In this embodiment, however, a diverter mechanism 384 includes two branches of unequal length. First branch 386 may be in line with a dispensing fluid channel 388, and second branch 390 may branch from the dispensing channel to take a more circuitous route before intersecting a sample channel 392 upstream of the first branch. In this embodiment, a dispensing fluid 394 may be released to pressurize branches 386 and 390 to trap and dispense a particle 396 travelling through channel 392.

Branches 386 and 390 may include any suitable arrangement of channels in which a path through branch 390 is substantially shorter than a path through branch 386, and in which branch 390 terminates at an intersection with channel 392 upstream and spaced from the intersection of branch 386 with channel 392. In this embodiment, branch 386 is configured as a straight path continuing in the direction of the long axis of channel 388. Branch 390 splits from channel 388 at a ninety-degree (or similar) angle, turning again after a certain distance to run parallel to branch 386 and intersect with channel 392. Accordingly, branch 390 forms a substantially longer path than branch 386.

Because the branches are of unequal length and substantially identical cross-section, fluid travelling down first branch 386 will reach an intersection with channel 392 before fluid travelling down second branch 390. Accordingly, flow in sample channel 392 will be effectively blocked by the incoming flow from first branch 386 (which will continue through the intersection and on through a dispensing channel 398). This action blocks the particle from proceeding to collection.

Dispensing fluid travelling down the second branch then intersects upstream of the blocked particle and flushes (e.g., carries or pushes) it through dispensing channel 398, along with a surrounding portion of the sample-containing carrier fluid. In this embodiment (among others), one or more valves or other control mechanisms for dispensing fluid may be located off-chip. In other words, diverter mechanism 384 may include no moving parts, and may be manufactured using conventional injection molding methods.

Diversion fluid channel 388, branch 386, and dispensing channel 398 may all be substantially aligned directionally at a right angle to sheathed sample channel 392. In other examples, various other angles and arrangements may be suitable.

FIG. 15 shows an embodiment of this Example 8 in the form of diverter mechanism 400, which is substantially similar to diverter mechanism 360 but with additional features. As in diverter mechanism 360, a cell-containing solution 402 flows through a sample channel 404 arranged transverse to a dispensing channel 406. Dispensing channel 406 contains a dispensing fluid 408 pressurized to a greater pressure than solution 402. Dispensing channel 406 also includes a branched section 410. However, in this embodiment, channel 406 forks into two symmetrical side channels 412 and 414 and a central channel 416 having a smaller cross section than the side channels. All three of the channels in the branched section are connected to sample channel 404. The respective liquids are configured to generally flow in the transverse directions as indicated by the arrows in the drawings.

A sensing region 418 is disposed in sample channel 404 upstream of the connection between branched section 410 and channel 404. As in the embodiment of FIG. 12, fluid 408 is normally prevented from interacting with solution 402 by one or more normally closed valves such as inlet valve 420. However, the embodiment of FIG. 15 does not include an outlet valve. Instead, a nozzle section 422 is formed in a distal end of dispensing channel 406 by narrowing the channel. This narrowing is configured to allow capillary action to resist leakage via the nozzle section during normal operation. A hydrophobic material may be added to nozzle section 422, such as by applying a coating, to further enhance this resistance.

Operation of the embodiment of FIG. 15 is similar to that of FIG. 12. However, two main differences exist during a diversion event. First, when valve 420 is opened, fluid 408 will flow through central channel 416 in addition to the side channels (412 and 414). Central channel 416 has a smaller cross section than the side channels, and therefore will allow a lower flow rate. This results in the confinement of a particle of interest 424 by the flows from the side channels as described above, but here includes an additional central flushing flow from the outlet of central channel 416. This may increase flushing efficiency and reduce dead zones.

Secondly, this embodiment does not include an outlet valve, instead relying on the capillary action of the nozzle section. Other embodiments may rely on the same functionality. When a diversion occurs, the pressure from the dispensing fluid released into the dispensing channel will overcome the capillary action and any hydrophobic coating, and dispense the particle through nozzle section 422. Accordingly, dispensing may occur only at pressures above a certain threshold, for example, above about 1 psi. This results in a reduction in manufacturing costs by eliminating a valve, and allows the amount of fluid dispensed with the particle to be controlled by operation of the inlet valve. The longer the inlet valve is open, the more fluid is dispensed. Typical volume of dispensed liquid may be from about 100 to about 1000 nL.

FIG. 16 shows another embodiment of this Example 8 in the form of diverter mechanism 430, which is substantially identical to diverter mechanism 400 of FIG. 15. However, diverter mechanism 430 includes two sensing regions and two dispensing channels, allowing the system to be used as a sorting device. In this embodiment, a first sensing region 432 is disposed along a sample channel 434 in series with a second sensing region 436. In some examples, the two sensing regions may be configured with different parameters to detect particles having different characteristics. In some examples, the two sensing regions may be configured with different sensing modalities.

Following the sensing regions, a series of two dispensing mechanisms in the form of first and second branched dispensing channels (438 and 440) and corresponding nozzle channels (442 and 444) are available to divert detected particles. Either dispensing mechanism may be tied to either sensing region through the controller.

For example, if a particle of interest 446 is detected by first sensing region 432 and meets a first set of criteria, the controller may respond by opening a valve 448 in second dispensing channel 440, thereby diverting particle 446 to dispense through nozzle channel 444. Likewise, a second particle meeting a second set of criteria may be detected by second sensing region 436 and sorted to a different destination by opening a valve 450 in first dispensing channel 438. In some examples, more than two sensing regions and/or more than two dispensing channels may be included. In some examples, a single dispensing channel may be used in conjunction with a movable substrate that is repositioned to sort into different wells or locations based on the detected particle characteristics. In some examples, a single sensing region may be configured to distinguish between particles meeting multiple sets of criteria.

Figure 17:
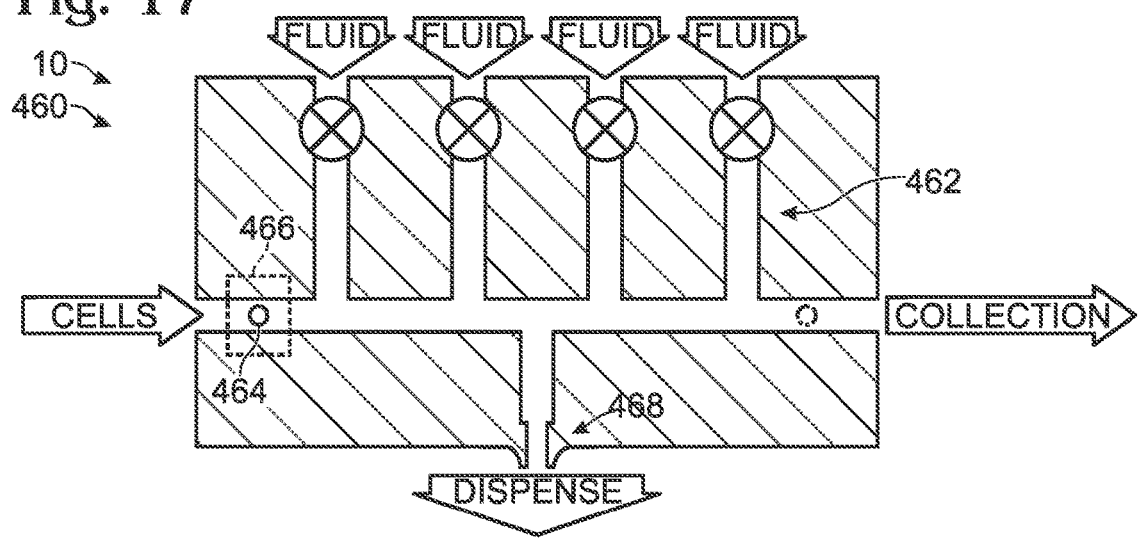
FIG. 17 shows another illustrative diverter mechanism suitable for use in the system shown in FIG. 1, including multiple parallel channels providing independent sources of pressurized dispensing fluid.

FIG. 17 shows another embodiment of this Example 8 in the form of diverter mechanism 460, which illustrates that dispensing is not limited to using a single pressure source for one or more channels, or to utilizing channel width to control the flow in each branch of a branched channel. Diverter mechanism 460 includes multiple dispensing fluid channels 462 having similar channel sizes. Each channel 462 may include an independent pressure source or control, such as a valve or throttling mechanism.

When a particle of interest 464 is detected by sensing region 466, the controller may then confine and direct particle 464 using any one of a combination of the pressure sources and pathways created by the independent channels 462. Various combinations may be utilized to maximize efficiency, speed, and/or to manipulate particles of differing characteristics. Particle 464 may be dispensed via nozzle 468 or sent to some other destination (not shown).

Figure 18:
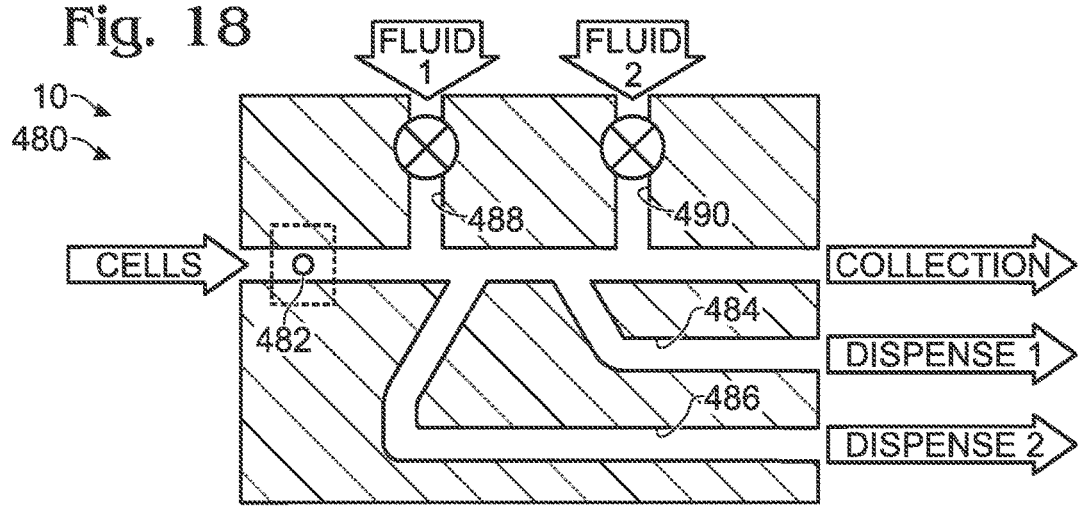
FIG. 18 shows another illustrative diverter mechanism suitable for use in the system shown in FIG. 1, including a sorting arrangement.

FIG. 18 shows another embodiment of this Example 8 in the form of diverter mechanism 480, which further illustrates the sorting feature explained with respect to FIG. 16. Depending on the properties of a detected particle 482, the particle can be directed to either a first dispensing channel 484 or a second dispensing channel 486 by activating either of the pressurized liquid sources 488 or 490, such as by opening one of the associated valves.

Figure 19:
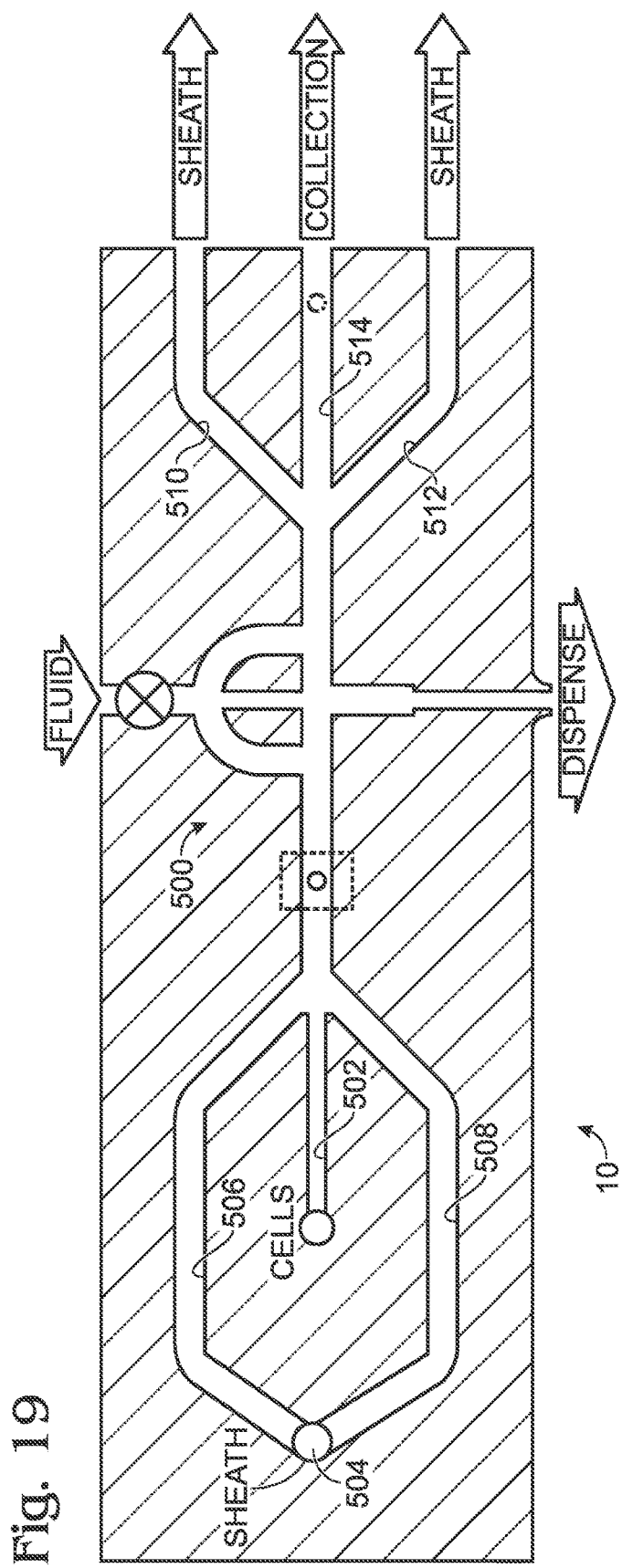
FIG. 19 shows another illustrative diverter mechanism suitable for use in the system shown in FIG. 1, including a sheathing and unsheathing channel arrangement for hydrodynamically focusing a cell sample.

FIG. 19 shows another embodiment of this Example 8 including a diverter mechanism 500 substantially identical to diverter mechanism 400. This embodiment illustrates one method for hydrodynamically focusing a solution channel 502 by introducing a sheathing liquid. The pressurized sheath liquid is introduced at an inlet port 504, and travels via sheathing channels 506 and 508 before intersecting with channel 502 to surround the solution contained in that channel. After detection and dispensing in diverter mechanism 500, the operation of which is explained above regarding diverter mechanism 400, the flow of liquid may enter an unsheathing area. In the unsheathing area, side channels 510 and 512 split off the outer flow of liquid from central channel 514, which then includes the original solution minus any dispensed volume. Unsheathing may be desirable to reduce the dilution of collected waste flow.

Example 9. Offset Channel Valved Diverter

Figure 20:
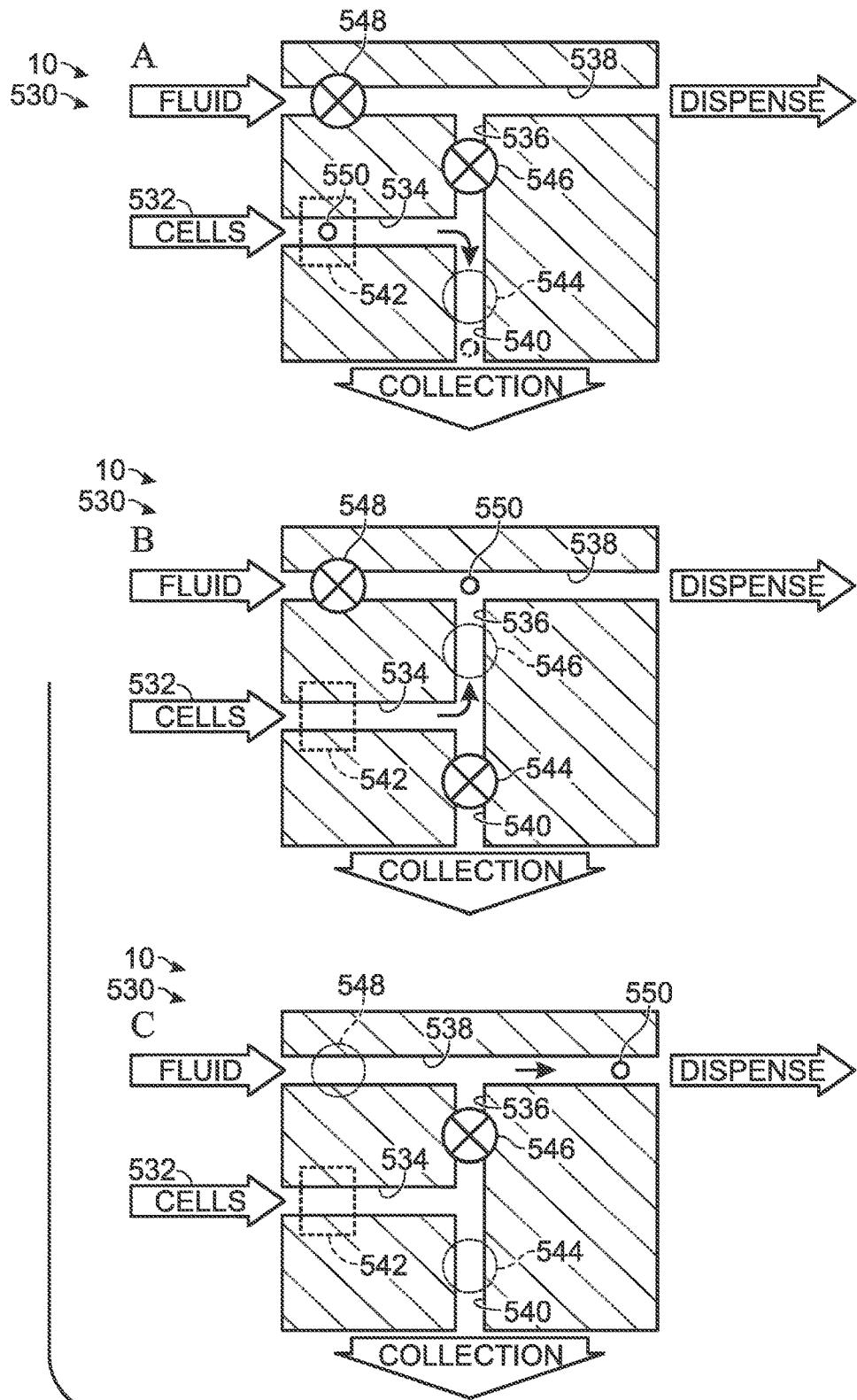
FIG. 20, Panels A-C, shows another illustrative diverter mechanism suitable for use in the system shown in FIG. 1, including an offset-tee arrangement with three valves.

This example describes offset channel valved diverters suitable for use in an on-demand cell dispensing system 10 according to the present disclosure; see FIGS. 20 and 21.

FIG. 20 shows an exemplary diverter mechanism 530 for use in system 10. Diverter mechanism 530 includes a pressurized cell-containing solution 532 in a sample channel 534. Sample channel 534 is connected via a valved connecting channel 536 with a selectively pressurizable dispensing channel 538, and via a valved collection channel 540 with a collection area. A sensing region 542 is disposed adjacent to sample channel 534 upstream of the connection between channel 534 and the other channels.

Three valves control the flows through diverter mechanism 530. A collection valve 544 is located in collection channel 540; a connection valve 546 is located in connecting channel 536; and a pressure source valve 548 is located in dispensing channel 538. As shown in Panel A of FIG. 20, collection valve 544 is normally open and the other two valves are normally closed to cause solution 532 to flow to the collection area.

When a particle of interest 550 is detected in sensing region 542, the controller responds by closing collection valve 544 and opening connection valve 546 to open a path to dispensing channel 538 as shown in Panel B of FIG. 20. Shortly thereafter, pressure source valve 548 is opened as shown in Panel C of FIG. 20 to pressurize channel 538 and flush particle 550 to the dispensing area. Connection valve 546 is closed at the same time to prevent backflow toward the sample channel and collection area. After a suitable delay, or upon confirmation that particle 550 was in fact diverted, the three valves are repositioned as needed to their original states in preparation for a subsequent diversion event.

FIG. 21 shows an exemplary diverter mechanism 560 for use in system 10. Diverter mechanism 560 is similar to diverter mechanism 530. However, in this embodiment, four valves are used rather than three. This avoids the situation of the previous embodiment in which the connection valve had to be closed to prevent backflow. Here, the four valves are operated in pairs to isolate and flush a particle.

Diverter mechanism 560 includes a cell-containing sample solution 564 in a sample channel 562. Sample channel 562 has two valves 566 and 568 arranged in series on either side of a diversion area. The diversion area is defined by a dispensing fluid inlet channel 570 and a dispensing fluid outlet channel 572, which is offset from the inlet on the opposite side of sample channel 562. Dispensing fluid inlet channel 570 includes an inlet valve 574, and dispensing fluid outlet channel 572 includes an outlet valve 576.

In this embodiment, valves 566 and 568 in sample channel 562 are normally open, and valves 574 and 576 in the dispensing channels are normally closed as shown in Panel A of FIG. 21. When a particle of interest 578 is detected in a sensing region 580 upstream of valve 566, the controller closes valves 566 and 568 to isolate the particle and opens valves 574 and 576 to flush the particle through dispensing fluid outlet channel 572 as shown in Panel B of FIG. 21.

Example 10. Forked Channel Diverter

This example describes a forked channel diverter suitable for use in an on-demand cell dispensing system 10 according to the present disclosure; see FIG. 22.

FIG. 22 show an exemplary diverter mechanism 600 for use in system 10. Diverter mechanism 600 includes a sample channel 602 intersected by sheath flow channels 604 and 606 similar to those described above with respect to FIG. 18. In this example, a particle of interest 608 detected at a sensing region 610 is diverted by simply closing off a collection fork 612 of channel 602 to redirect the particle to a dispensing fork 614 of channel 602 as shown in Panel B of FIG. 22. No additional pressure source in the form of dispensing fluid is used. In some embodiments, such as the one shown in Panels A and B of FIG. 22, a valve 616 is used to close off collection fork 612. Alternatively or additionally, a valve may be included in the dispensing fork. In some examples, a toggle valve may be used to selectively close and open the two forks simultaneously.

Example 11. System

Figure 23:
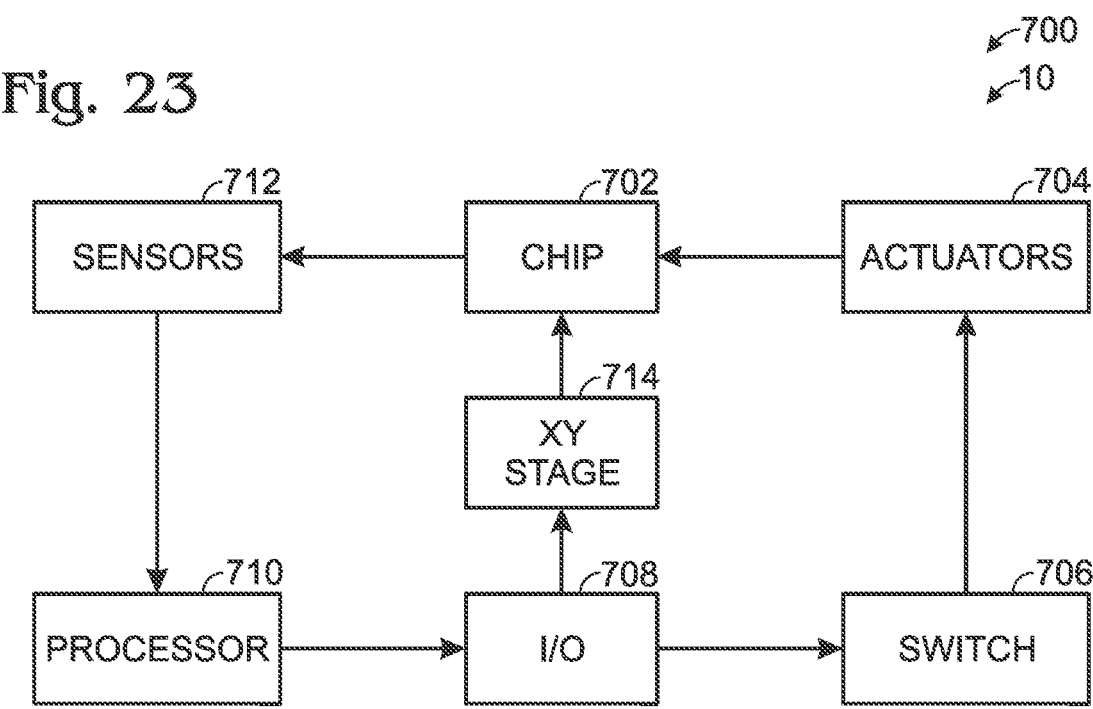
FIG. 23 shows an illustrative embodiment of the system shown in FIG. 1, including a control system and substrate positioning mechanism.

This example describes an on-demand cell dispensing system 700 according to the present disclosure; see FIG. 23.

FIG. 23 is a schematic diagram showing an illustrative system 700 which is an example of system 10. System 700 includes a microfluidics chip 702 on which is located a system including the channels and one or more diverter mechanisms described above. Various devices such as valves, sliders, vacuum chambers, and other components that may be located on chip 702 are caused to operate by actuators 704 such as solenoid valves. These actuators 704 are in turn activated by switches 706 controlled through an input/output (I/O) system 708 by a processor 710. Processor 710 may include a microprocessor such as the processor of a typical personal computer or similar device, and may be in communication with a memory or storage device containing instructions for the processor to carry out. The controller described above may include the combination of processor 710 and the storage device.

Processor 710 receives input from sensors 712, such as a camera system or other detection device used in a sensing region on the chip. Chip 702 may be mounted on or associated with an X-Y stage 714 such that the chip or a substrate onto which the chip dispenses particles can be precisely located and repositioned as desired.

Example 12. Selected Embodiments

This section describes additional aspects and features of on-demand particle dispensing systems, presented without limitation as a series of paragraphs, some or all of which may be alphanumerically designated for clarity and efficiency. Each of these paragraphs can be combined with one or more other paragraphs, and/or with disclosure from elsewhere in this application, including the materials incorporated by reference in the Cross-References, in any suitable manner. Some of the paragraphs below expressly refer to and further limit other paragraphs, providing without limitation examples of some of the suitable combinations.

Selected Embodiments I

Paragraph 1. A method of isolating a particle from a fluid sample, the method comprising: (A) streaming a fluid sample containing a particle through a microfluidic sample channel; and (B) diverting the particle from the sample channel into an outlet channel, based on a detected characteristic of the particle, by directing a diverting fluid into the sample channel upstream and downstream of the particle.

Paragraph 2. The method of paragraph 1, wherein the diverting fluid is directed into the sample channel at a substantially right angle.

Paragraph 3. The method of any one of paragraphs 1-2, wherein the diverting fluid is directed into the sample channel upstream and downstream of the particle non-simultaneously, such that the downstream diverting fluid blocks flow from proceeding in the sample channel and the upstream diverting fluid pushes the particle toward the outlet channel.

Paragraph 4. The method of any one of paragraphs 1-3, wherein the downstream diverting fluid is directed into the sample channel at a location opposite an intersection of the sample channel and the outlet channel.

Paragraph 5. The method of any one of paragraphs 1-4, further including detecting the characteristic of the particle by measuring an optical signal from a detection zone through which the particle travels.

Paragraph 6. The method of any one of paragraphs 1-5, further including detecting the characteristic of the particle by measuring an electrical signal from a detection zone through which the particle travels.

Paragraph 7. The method of any one of paragraphs 1-6, further comprising dispensing the particle from the outlet channel.

Paragraph 8. A method of isolating a particle from a fluid sample, the method comprising: streaming a fluid sample containing a particle through a sample channel having a detection zone and a diversion zone; detecting a characteristic of the particle as it passes through the detection zone; generating a diversion signal in response to the detected characteristic satisfying one or more selected criteria; and diverting the particle from the sample channel into an outlet channel, in response to the diversion signal, thereby substantially isolating the particle from the sample, by directing a diverting fluid into the sample channel upstream and downstream of the particle and flushing the particle into the outlet channel.

Paragraph 9. The method of paragraph 8, wherein streaming the fluid sample through a sample channel includes adding a sheathing fluid to the sample channel at a location downstream from where the fluid sample is introduced to the sample channel.

Paragraph 10. The method of any one of paragraphs 8-9, wherein the sheathing fluid biases the fluid sample toward the center of the sample channel.

Paragraph 11. The method of any one of paragraphs 8-10, the sample fluid containing a first and a second type of particle, wherein detecting a characteristic of the particle distinguishes between the first and second types of particle, and wherein the particle is diverted from the sample channel if it is the first type of particle.

Paragraph 12. The method of paragraph 11, further including generating a second diversion signal in response to the detected characteristic indicating that the particle is the second type; and diverting the particle from the sample channel into a second outlet channel, in response to the second diversion signal.

Paragraph 13. The method of any one of paragraphs 8-11, wherein direction of the diverting fluid includes directing the diverting fluid into the sample channel first downstream and then upstream of the particle, such that the particle is blocked by the downstream diverting fluid and then flushed by the upstream diverting fluid into the outlet channel.

Paragraph 14. The method of paragraph 13, wherein sequencing of the downstream and upstream diverting fluid includes passing the diverting fluid through a downstream branch and an upstream branch of a diverting fluid channel, wherein the downstream branch forms a shorter pathway to the sample channel than the upstream branch.

Paragraph 15. The method of paragraph 13, wherein the downstream branch and the outlet channel intersect the sample channel on substantially opposite sides such that the downstream branch and the outlet channel are generally aligned with each other.

Paragraph 16. A method of isolating a particle from a fluid sample, the method comprising: directing a fluid sample containing a particle through a sample channel and past a detection zone; detecting the particle as it passes the detection zone; and directing a diverting fluid into the sample channel, upstream and downstream of the particle, such that the particle is directed into an outlet channel separate from the sample channel.

Paragraph 17. The method of paragraph 16, wherein directing the diverting fluid into the sample channel includes blocking the particle from continuing through the sample channel using a downstream introduction of diverting fluid and then flushing the particle into the outlet channel using an upstream introduction of diverting fluid.

Paragraph 18. The method of paragraph 17, wherein the diverting fluid is directed into the sample channel through a diverting fluid channel divided into a first distributary and a second distributary having a greater length than the first distributary.

Paragraph 19. The method of paragraph 18, wherein the second distributary intersects the sample channel upstream of the outlet channel.

Paragraph 20. The method of paragraph 19, wherein the first distributary intersects the sample channel at a location substantially opposite an intersection between the sample channel and the outlet channel.

Selected Embodiments II

Paragraph A. A method of isolating a particle from a fluid sample, the method comprising (1): streaming the fluid sample containing the particle through a sample channel; and (2) diverting the particle from the sample channel into an outlet channel, based on a characteristic of the particle, by directing a diverting fluid into the sample channel upstream and downstream of the particle.

Paragraph B. A method of isolating a particle from a fluid sample, the method comprising: (1) streaming the fluid sample containing the particle through a sample channel having a detection zone and a diversion zone; (2) detecting a characteristic of the particle as it passes through the detection zone; (3) generating a diversion signal if the detected characteristic satisfies a preselected criterion; and (4) diverting the particle from the sample channel into an outlet channel, thereby isolating the particle from the sample, by directing a diverting fluid into the sample channel upstream and downstream from the outlet channel, in response to the diversion signal.

Paragraph C. A method of isolating a particle from a fluid sample, the method comprising: (1) directing the fluid sample containing the particle through a sample channel; (2) detecting the particle as it passes in the sample channel through a detection zone; and (3) diverting the particle from the sample channel into an intersecting outlet channel as the particle passes near the outlet channel, thereby isolating the particle from the sample, by directing a dispensing fluid into the sample channel upstream and downstream from the outlet channel, in response to a signal generated during the step of detecting, such that the particle is directed into the outlet channel.

Paragraph D. A method of isolating a particle from a fluid sample, the method comprising: (1) directing the fluid sample containing the particle through a sample channel; (2) detecting the particle as it passes in the sample channel through a detection zone; and (3) directing a dispensing fluid into the sample channel, upstream and downstream from the particle, in response to a signal from the detection zone, such that the particle is directed into an outlet channel, separate from the sample channel, and positioned between the upstream and downstream sites where the dispensing fluid is directed into the sample channel.

Paragraph E. A method of isolating a particle from a fluid sample, the method comprising: (1) directing the fluid sample containing the particle through a sample channel and past a detection zone; (2) detecting the particle as it passes the detection zone; and (3) directing a dispensing fluid into the sample channel, upstream and downstream from the particle, such that the particle is directed into an outlet channel, separate from the sample channel.

Paragraph 1. The method of any of paragraphs A to E, wherein the diverting fluid is directed into the sample channel at a substantially right angle.

Paragraph 2. The method of any of paragraphs A to E, wherein the diverting fluid is directed into the sample channel upstream and downstream from the outlet channel in at least partially opposing directions, to bracket the particle and push it toward the outlet channel.

Paragraph 3. The method of any preceding paragraph, wherein the step of detecting the particle (or a characteristic of the particle) includes a step of measuring an optical signal from the detection zone.

Paragraph 4. The method of paragraph 3, wherein the optical signal is an absorbance of light by the particle.

Paragraph 5. The method of paragraph 3, wherein the optical signal is a scattering of light by the particle.

Paragraph 6. The method of paragraph 3, wherein the optical signal is a luminescence emitted by the particle.

Paragraph 7. The method of paragraph 3, wherein the optical signal is an image of the particle.

Paragraph 8. The method of any of paragraphs A to 2, wherein the step of detecting the particle includes a step of measuring an electrical signal from the detection zone.

Paragraph 9. The method of paragraph 8, wherein the electrical signal is a change in impedance caused by the particle.

Paragraph 10. The method of paragraph 8, wherein the electrical signal is a change in capacitance caused by the particle.

Paragraph 11. The method of any preceding paragraph, further comprising dispensing the particle from the outlet channel.

Paragraph 12. The method of paragraph 11, wherein the step of dispensing the particle includes ejecting a droplet containing the particle and diverting fluid from the outlet channel and into a reservoir.

Paragraph 13. The method of any preceding paragraph, wherein the step of streaming the fluid sample through a sample channel includes a step of adding a sheathing fluid to the sample channel, downstream from where the sample is added.

Paragraph 14. The method of paragraph 13, wherein the sheathing fluid surrounds the particle and biases it toward the center of the sample channel.

Paragraph 15. The method of paragraph 13, further comprising a step of removing at least a portion of the sheathing fluid from the sample channel after the particle has passed the diversion zone.

Paragraph 16. The method of any preceding paragraph, the sample containing at least two types of particles, wherein the step of detecting the particle distinguishes between the at least two types of particles, and wherein the step of diverting the particle is performed on only one type of particle to separate the one type of particle from the other types of particles.

Paragraph 17. The method of any of paragraphs A to 15, the sample containing at least two types of particles, further comprising a step of sorting the two types of particles by diverting one type of particle at the diversion zone and by allowing the remaining types of particles to continue in the sample channel.

Paragraph 18. The method of paragraph 17, wherein the step of sorting the two types of particles further comprises a step of diverting another type of particle at a second diversion zone.

Paragraph 19. The method of paragraph 18, further comprising allowing any remaining types of particles to continue in the sample channel.

Paragraph 20. The method of any of paragraphs 16 to 19, wherein the at least two types of particles are distinguished by size.

Paragraph 21. The method of any of paragraphs 16 to 19, wherein the at least two types of particles are distinguished by cell type.

Paragraph 22. The method of paragraph 21, wherein cell type is selected from the group consisting of diseased and healthy (e.g., cancerous and noncancerous), prokaryotes and eukaryotes, transformed and nontransformed, and wild type and mutant.

Paragraph 23. The method of any of paragraphs 16, wherein the at least two types of particles are distinguished by a signal from an indicator.

Paragraph 24. The method of any preceding paragraph, further comprising diluting the sample to increase the average distance between particles as the particles are directed through the sample channel.

Paragraph 25. The method of paragraph 24, wherein the sample fluid is diluted at least in part while the sample is in the sample channel.

Paragraph 26. The method of any preceding paragraph, the outlet channel being separated from the sample channel by an outlet valve, wherein the step of diverting the particle includes a step of opening the outlet valve while diverting fluid is directed into the sample channel, allowing the particle to move past the valve and into the outlet channel.

Paragraph 27. The method of paragraph 26, further comprising closing the outlet valve after the step of diverting the particle.

Paragraph 28. The method of paragraph 26 or 27, wherein the valve is actuated externally.

Paragraph 29. The method of paragraph 28, wherein the valve is actuated by at least one of a solenoid actuator and a pinch valve, a piezoelectric actuator and a pinch valve, a magnetic actuator and a pinch valve, and a magnetic toggle valve.

Paragraph 30. The method of any preceding paragraph, wherein the diverting fluid is directed into the sample channel independently upstream and downstream of the outlet channel.

Paragraph 31. The method of any of paragraphs A to 29, wherein the pressure exerted by the diverting fluid as it is directed into the sample channel is independently controlled upstream and downstream of the outlet channel.

Paragraph 32. The method of any preceding paragraph, wherein the diverting fluid is directed into the sample channel by dividing a diverting channel into at least two distributaries, at least one of the distributaries intersecting the sample channel upstream from the outlet channel, and at least one of the distributaries intersecting the sample channel downstream from the outlet channel.

Paragraph 33. The method of any preceding paragraph, further comprising a step of collecting the sample, including any undiverted particles, after the sample has passed the detection zone and the diversion zone.

Paragraph 34. The method of any preceding paragraph, wherein the step of diverting the particle further includes directing the diverting fluid into the sample channel directly across from the outlet channel, in addition to upstream and downstream from the outlet channel.

Paragraph 35. The method of any preceding paragraph, wherein the step of diverting the particle further includes directing the diverting fluid into the sample channel at an additional position upstream or downstream from the outlet channel.

Paragraph 36. The method of paragraph 35, wherein the step of diverting the particle further includes directing the diverting fluid into the sample channel at at least two positions both upstream and downstream from the outlet channel.

Paragraph 37. The method of any preceding paragraph, wherein the detection zone is upstream from the detection zone and there is a delay between when the particle is detected and when the diverting fluid is directed to allow for movement of the particle through the sample channel from the detection zone to the diversion zone.

Paragraph 38. The method of any of paragraphs A to 36, wherein the detection zone and the diversion zone are coincident.

Paragraph 39. The method of any preceding paragraph, the detection zone and the diversion zone being a first detection zone and a first diversion zone, respectively, further comprising repeating the step of detecting the particle at a second detection zone and repeating the step of diverting the particle at a second diversion zone.

Paragraph 40. The method of any preceding paragraph, the outlet channel including a dispensing orifice sufficiently small that fluid does not exit the outlet channel unless and until the diverting fluid is directed into the sample channel, increasing fluid pressure at the orifice.

Paragraph 41. The method of any preceding paragraph, wherein the particle includes at least one of a cell, an isolated organelle, a virus, a bead, a droplet, and a vesicle.

Paragraph 42. The method of any of paragraphs A to 40, wherein the particle is an impurity and thus the fluid sample remaining in the sample channel after the particle is diverted is at least partially purified.

Paragraph 43. The method of any preceding paragraph, wherein the diameter of the particles is no larger than about 100 microns, 50 microns, 25 microns, 10 microns, 5 microns, 2 microns, or 1 micron, among others.

Paragraph 44. The method of any preceding paragraph, further comprising concentrating the cells to the center of the sample channel and/or increasing the spacing between cells by hydrodynamic focusing.

Paragraph 45. The method of any preceding paragraph, further comprising a step of applying pressure to the fluid sample and/or the diverting fluid to induce their movement (e.g., using one or more pumps).

Paragraph 46. The method of any preceding paragraph, wherein the step of detecting a particle includes measuring an optical signal (e.g., fluorescence, or forward or side scatter signals), an electrical signal (e.g., impedance), an electromagnetic signal (e.g., by detecting ferrous particles), and/or a chemical signal.

Paragraph 47. The method of any preceding paragraph, wherein the step of detecting a particle includes sensing the particle using at least one of the Coulter Principle, a capacitance sensor, a photomultiplier tube (PMT), a digital area camera (e.g., CCD or CMOS, among others), a line scan camera, and a photodiode.

Paragraph 48. The method of any preceding paragraph, wherein the channels for trapping and dispensing are symmetric (for practical chip design).

Paragraph F. A system for isolating a particle from a fluid sample, the system comprising:
- a channel network including a sample channel for conveying the fluid sample, an inlet channel intersecting the sample channel for introducing diverting fluid into the fluid sample, an outlet channel for receiving a particle from the fluid sample, and a collection port for receiving sample after the particle has been diverted;
- a detector configured to detect particles in the fluid sample as the sample moves in the sample channel through a detection zone; and
- a diverter mechanism, coincident with or downstream from the detector, configured to divert the particle from the sample channel into the outlet channel, in response to a signal from the detector, by directing diverting fluid through the inlet channel and into the sample channel, upstream and downstream from the outlet channel, urging the particle into the outlet channel.

Selected Embodiments III

Paragraph 1. An on-demand particle dispensing system configured for attachment to an instrument, the system comprising:
 a. a microfluidic chip
 b. a detection area
 c. a dispensing area, and
 d. a nozzle channel
wherein the dispensing area is configured to connect to an actuation mechanism for confining and dispensing a bulk of liquid.

Paragraph 2. The system of paragraph 1, wherein particles are confined and then dispensed along with a bulk of liquid.

Paragraph 3. The system of paragraph 2, where confining section allows for manufacturing and operational tolerances not to have adverse effect on the performance.

Paragraph 4. The system of paragraph claim 3, further comprising an alignment feature such as one or more apertures for attaching the system to an instrument.

Paragraph 5. The system of paragraph 1, 2, 3, or 4, further comprising a feature before collection to un-sheath the sample to reduce or prevent dilution of the sample.

Paragraph 6. The system of paragraph 1, which can detect particles, optically, electrically, electromagnetically, or a combination of any of them.

Paragraph 7. The system of paragraph 1, which can have multiple dispensing zones to dispense particles or cells with different properties.

Paragraph 8. The system of paragraph 1, which has hydrodynamic focusing for proper separation and alignment of particles.

Paragraph 9. The system of paragraph 1, which in conjunction with an x-y motion system can dispense one or multiple particles onto a specified location.

Paragraph 10. The system of paragraph 1, which utilizes one or multiple independent pressure sources for confining and dispensing particle(s) or cell(s) of interest.

Paragraph 11. The system of paragraph 1, where the chip is made of two layers, one being a plastic chip with channels and the other a laminate or another layer of suitable material.

Paragraph 12. The system of paragraph 1, where the sample port can have either a pre-attached tube which can be inserted directly into a sample source or an on board reservoir to avoid cross contamination.

Paragraph 13. The system of paragraph 1, which can be reconfigured to be used as a particle or cell sorter.

Paragraph 14. The system of paragraph 1, where the nozzle channel comprises a narrow section at the end to provide sufficient capillary pressure to prevent leakage unless and until dispensing fluid is directed into the system.

15. The system of paragraph 14, where the nozzle channel also comprises a wide section to allow for flow of liquid with minimal resistance.

Paragraph 16. The system of paragraph 14 or 15, where the nozzle channel also comprises a coating to increase the capillary pressure.

Paragraph 17. An on-demand particle dispensing method comprising:
 a. a microfluidic chip
 b. a detection area
 c. a dispensing area, and
 d. a nozzle channel
wherein the dispensing area is configured to connect to an actuation mechanism for confining and dispensing a bulk of liquid.

Paragraph 18. The system of paragraph 17, wherein particles are confined and then dispensed along with a bulk of liquid.

Paragraph 19. The system of paragraph 18, where confining section allows for manufacturing and operational tolerances not to have adverse effect on the performance.

Paragraph 20. The system of paragraph 17, further comprising alignment feature.

Paragraph 21. The system of paragraph 17, 18, or 19, with a feature before collection to un-sheath the sample to prevent dilution of the sample.

Paragraph 22. The system of paragraph 17, which can detect particles, optically, electrically, electromagnetically, or a combination of any of them.

Paragraph 23. The system of paragraph 17, which can have multiple dispensing zones to dispense particles or cells with different properties.

Paragraph 24. The system of paragraph 17, which has hydrodynamic focusing for proper separation and alignment of particles.

Paragraph 25. The system of paragraph 17, which in conjunction with an x-y motion system can dispense one or multiple particles onto a specified location.

Paragraph 26. The system of paragraph 17, which utilizes one or multiple independent pressure sources for confining and dispensing particle(s) or cell(s) of interest.

Paragraph 27. The system of paragraph 17, where the chip is made of two layers, one being a plastic chip with channels and the second one a laminate or another layer of suitable material.

Paragraph 28. The system of paragraph 17, where the sample port can have either a pre-attached tube which can be inserted directly into a sample source or an on-board reservoir to avoid cross contamination.

Paragraph 29. The system of paragraph 17, where the nozzle channel comprises a narrow section at the end to provide sufficient capillary pressure to prevent leakage.

Paragraph 30. The system of paragraph 29, where the nozzle channel also comprises a wide section to allow for flow of liquid with minimal resistance.

Paragraph 31. The system of paragraph 29 or 30, where the nozzle channel also comprises a coating to increase the capillary pressure.

Selected Embodiments IV

This subsection presents selected embodiments of the present disclosure, described as a third series of numbered paragraphs.

Paragraph 1. An on-demand particle dispensing system configured for attachment to an instrument, said system including a microfluidic chip comprising:
   a. a sample channel
   b. an inducible dispensing channel
   c. a detection area
   d. a dispensing area, and
   e. a nozzle channel
wherein the dispensing channel is split into multiple distributaries that intersect the sample channel at said dispensing area, said intersection configured such that, when induced, dispensing liquid from the multiple distributaries from the dispensing channel is forced through the intersection with the sample channel into the nozzle channel, this flow also forcing the contents of a portion of the sample channel, between the most upstream and most downstream distributaries of the dispensing channel, into the nozzle channel with the dispensing liquid, said intersection further configured such that when flow in the dispensing channel is not induced, liquid in the sample channel flows through the dispensing area to a sample collection area.

Paragraph 2. The system of paragraph 1, wherein particles from the sample channel are confined and dispensed along with a bulk of dispensing liquid.

Paragraph 3. The system of paragraph 1, wherein particles may be detected in the detection area creating a signal that may induce flow in the dispensing channel, and subsequent confinement and dispensing of particles from the sample channel.

Paragraph 4. The system of paragraph 1, wherein the induction of flow from the dispensing channel is synchronized with the signal from the detection area so that a particle generating a signal in the detection area is confined and dispensed once it has traveled to the dispensing area.

Paragraph 5. The system of paragraph 1, which has hydrodynamic focusing upstream of the detection area for proper separation and alignment of particles.

Paragraph 6. The system of paragraph 1, with a feature before sample collection to un-sheath the sample to prevent dilution of the sample.

7. The system of paragraph 1, which can detect particles, optically, electrically, electromagnetically, or a combination of any of them.

Paragraph 8. The system of paragraph 1, wherein flow from the nozzle channel containing particles of interest may be collected by a suitable vessel.

Paragraph 9. The system of paragraph 1, wherein the nozzle channel includes a wide section adjacent to the dispensing area to allow for flow of liquid with minimal resistance.

Paragraph 10. The system of paragraph 1, wherein the nozzle channel includes a narrow section at the end furthest from the dispensing area to provide sufficient capillary pressure to prevent leakage.

Paragraph 11. The system of paragraph 1, wherein the nozzle channel includes a coating to increase the capillary pressure.

Paragraph 12. The system of paragraph 1, which can have multiple dispensing areas to dispense particle{s} with different properties.

Paragraph 13. The system of paragraph 1, which utilizes one or multiple independent dispensing fluid sources for confining and dispensing particle{s} of interest.

Paragraph 14. The system of paragraph 1, which in conjunction with an x-y motion system can dispense one or multiple particles via the nozzle channel onto a specified location.

Paragraph 15. The system of paragraph 1, wherein the microfluidic chip is made of two layers, one layer being plastic with channels formed into it, and the other a laminate or another layer of suitable material.

Paragraph 16. The system of paragraph 1, wherein the sample port can have either a pre-attached tube which can be inserted directly into a sample source or an on board reservoir to avoid cross contamination.

Paragraph 17. The system of paragraph 1, further including an alignment feature for proper positioning of the microfluidic chip.

Paragraph 18. The system of paragraph, where confining section allows for manufacturing and operational tolerances not to have adverse effect on the performance.

Paragraph 19. The system of paragraph 1 which can be reconfigured to be used as a particle or cell sorter.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A system for diverting a particle from a fluid sample, the system comprising:
   a channel network including
      a sample channel having an upstream region, a downstream region, and an intermediate region extending between the upstream and downstream regions,
      a pair of inlet channels intersecting the sample channel at an upstream end and a downstream end of the intermediate region of the sample channel, and
      an outlet channel intersecting the intermediate region of the sample channel;
   a pressure source operatively connected to the pair of inlet channels;
   a detector configured to detect a signal from a particle in a fluid sample flowing in the upstream region of the sample channel; and a controller configured to create a diversion signal, if the signal detected from the particle meets one or more criteria;

wherein the diversion signal activates the pressure source to urge diverting fluid into the sample channel from the pair of inlet channels, while the particle is located in the intermediate region of the sample channel, such that the particle is flushed out of the sample channel via the outlet channel.

2. The system of claim 1, wherein the channel network includes a branched channel including a branched section forming an upstream branch and a downstream branch, wherein the upstream branch and the downstream branch are the pair of inlet channels, and wherein the downstream branch forms a shorter pathway to the sample channel than the upstream branch.

3. The system of claim 1, wherein at least one of the inlet channels intersects the sample channel at a substantially right angle.

4. The system of claim 1, wherein the diversion signal causes diverting fluid to be urged into the sample channel at the upstream end and the downstream end non-simultaneously, such that the diverting fluid at the downstream end blocks flow from proceeding in the sample channel, and such that the diverting fluid at the upstream end pushes the particle toward the outlet channel.

5. The system of claim 1, wherein the inlet channel intersecting the sample channel at the downstream end of the intermediate region is aligned with the outlet channel.

6. The system of claim 1, wherein the detector is a photodetector.

7. The system of claim 1, further comprising at least one valve that is adjusted in response to the diversion signal, to activate the pressure source.

8. The system of claim 7, further comprising a microfluidic chip that defines each of the channels, wherein the at least one valve is spaced from the microfluidic chip.

9. The system of claim 7, wherein the at least one valve includes one or more valves that open in response to the diversion signal, to create fluid communication between the pressure source and each of the inlet channels.

10. The system of claim 1, wherein the channel network includes a sheath channel configured to add sheathing fluid to the sample channel at a location in the upstream region.

11. The system of claim 1, further comprising a microfluidic chip that defines the channel network, wherein the diversion signal causes the particle to be dispensed from the microfluidic chip.

12. The system of claim 1, wherein the outlet channel is a nozzle channel having a wide section proximal to the sample channel and a narrow section distal to the sample channel, and wherein the narrow section is configured to provide sufficient capillary pressure to prevent leakage.

13. The system of claim 1, wherein the outlet channel includes a coating to increase capillary pressure.

14. The system of claim 1, further comprising a source of diverting fluid connected to the pair of inlet channels.

15. The system of claim 1, wherein the pressure source includes a pump.

16. The system of claim 1, further comprising a microfluidic chip defining the channel network, wherein the microfluidic chip is made of a first layer and a second layer, wherein the first layer has a surface in which each of the channels is formed, and wherein the second layer is bonded to the first layer to cover each of the channels.

* * * * *